United States Patent
Suzuki

(10) Patent No.: US 11,612,653 B2
(45) Date of Patent: Mar. 28, 2023

(54) ANTI-TUMOR AGENT CONTAINING IMMUNOMODULATOR, AND ANTITUMOR EFFECT POTENTIATOR

(71) Applicant: TAIHO PHARMACEUTICAL CO., LTD., Chiyoda-ku (JP)

(72) Inventor: Norihiko Suzuki, Tokushima (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 233 days.

(21) Appl. No.: 16/068,573

(22) PCT Filed: Jan. 6, 2017

(86) PCT No.: PCT/JP2017/000266
§ 371 (c)(1),
(2) Date: Jul. 6, 2018

(87) PCT Pub. No.: WO2017/119484
PCT Pub. Date: Jul. 13, 2017

(65) Prior Publication Data
US 2019/0046639 A1 Feb. 14, 2019

(30) Foreign Application Priority Data

Jan. 8, 2016 (JP) .............................. JP2016-002463
Jun. 15, 2016 (JP) .............................. JP2016-119117

(51) Int. Cl.

| | |
|---|---|
| *A61K 39/395* | (2006.01) |
| *A61K 31/506* | (2006.01) |
| *A61K 31/7072* | (2006.01) |
| *A61K 45/06* | (2006.01) |
| *C07K 16/28* | (2006.01) |
| *A61P 35/00* | (2006.01) |
| *A61K 31/44* | (2006.01) |
| *A61K 31/53* | (2006.01) |
| *A61K 39/00* | (2006.01) |

(52) U.S. Cl.
CPC .......... *A61K 39/3955* (2013.01); *A61K 31/44* (2013.01); *A61K 31/506* (2013.01); *A61K 31/53* (2013.01); *A61K 31/7072* (2013.01); *A61K 39/39541* (2013.01); *A61K 45/06* (2013.01); *A61P 35/00* (2018.01); *C07K 16/2818* (2013.01); *A61K 2039/505* (2013.01)

(58) Field of Classification Search
CPC ................ A61K 39/3955; A61K 45/06; A61K 39/39541; A61K 31/44; A61K 31/53; A61K 31/506; A61K 31/7072; A61K 2039/505; A61K 31/513; A61K 39/395; A61K 2300/00; C07K 16/2818; A61P 35/00; A61P 37/02
See application file for complete search history.

(56) References Cited

U.S. PATENT DOCUMENTS

| | | |
|---|---|---|
| 5,744,475 A | 4/1998 | Yano et al. |
| 6,159,969 A | 12/2000 | Yano et al. |
| 6,294,535 B1 | 9/2001 | Yano et al. |
| 2006/0110383 A1 | 5/2006 | Honjo et al. |
| 2006/0167031 A1 | 7/2006 | Emura et al. |
| 2010/0203056 A1 | 8/2010 | Irving et al. |
| 2011/0082163 A1 | 4/2011 | Fukuoka et al. |
| 2012/0121604 A1 | 5/2012 | Jure-Kunkel et al. |
| 2012/0225838 A1 | 9/2012 | Fukuoka et al. |
| 2015/0320859 A1 | 11/2015 | Maecker et al. |

FOREIGN PATENT DOCUMENTS

| | | |
|---|---|---|
| CN | 103788075 A | 5/2014 |
| CN | 103788075 B | 3/2018 |
| JP | 2007-277242 A | 10/2007 |
| JP | 2012-511329 A | 5/2012 |
| JP | 2012-219062 A | 11/2012 |
| JP | 2012-533619 A | 12/2012 |
| WO | WO 96/30346 A1 | 10/1996 |
| WO | WO 2004/004771 A1 | 1/2004 |
| WO | WO 2006/080327 A1 | 8/2006 |
| WO | WO 2007/113648 A2 | 10/2007 |
| WO | WO 2009/147843 A1 | 12/2009 |
| WO | WO 2011/065541 A1 | 6/2011 |
| WO | WO 2013/181452 A1 | 12/2013 |
| WO | WO 2015/009856 A2 | 1/2015 |
| WO | WO 2015/034032 A1 | 3/2015 |
| WO | WO 2015/069571 A1 | 5/2015 |
| WO | WO 2015/077717 A1 | 5/2015 |

OTHER PUBLICATIONS

Mayer et al., Randomized trial of TAS-102 for refractory metastatic colorectal cancer. The New England Journal of Medicine 372: 1909-1919, May 14, 2015.*
Norihiko Suzuki et al. Efficacy of trifluridine/tipiracil + anti-mouse PD-1 antibody combination on mouse colorectal cancer model and related tumor immunomodulatory effects [abstract]. In: Proceedings of the American Association for Cancer Research Annual Meeting 2017; Apr. 1-5, 2017.*
Lee et al., Table 1 from (Transl. Lung Cancer Res. 3(6): 408-410, Dec. 2014).*
Iams et al. (My Cancer Genome, pp. 1-5, Nov. 24, 2015).*
Berdis Frontiers in Molecular Biosciencnes 4(78): 1-11, published Nov. 21, 2017.*

(Continued)

*Primary Examiner* — Alana Harris Dent
(74) *Attorney, Agent, or Firm* — Oblon, McClelland, Maier & Neustadt, L.L.P.

(57) ABSTRACT

Provided is a novel cancer treatment method with less side effects, showing remarkably excellent antitumor effect.

An antitumor agent is used for administering a DNA function inhibitor and an immunomodulator in combination.

54 Claims, 14 Drawing Sheets

(56) References Cited

OTHER PUBLICATIONS

European Search Report dated Jul. 19, 2019 in European Patent Application No. 17736021.1, 17 pages.
Stewart, R., et al., "Identification and Characterization of MEDI4736, an Antagonistic Anti-PD-L1 Monoclonal Antibody", Cancer Immunology Research, vol. 3, No. 9, Sep. 1, 2015, XP055247766, pp. 1052-1062 with cover page.
Takeo, N., et al.. "Clinical Significance and Therapeutic Potential of the Programmed Death-1 Ligand/Programmed Death-1Pathway in Human Pancreatic Cancer", Clin Cancer Res 2007, vol. 13 No. 7, XP002533527, pp. 2151-2157.
De Sousa Cavalcante, L., et al., "Gemcitabine: Metabolism and molecular mechanisms of action, sensitivity and chemoresistance in pancreatic cancer", European Journal of Pharmacology, vol. 741, Jul. 30, 2014, XP029050433, pp. 8-16.
Nukatsuka, M., et al., "Efficacy of Combination Chemotherapy Using a Novel Oral Chemotherapeutic Agent, TAS-102, with Irinotecan Hydrochloride on Human Colorectal and Gastric Cancer Xenografts", Anticancer Research, Mar. 2015, vol. 35, No. 3, XP002792829, pp. 1437-1445.
Tsukihara, H., et al., "Efficacy of combination chemotherapy using a novel oral chemotherapeutic agent, TAS-102, together with bevacizumab, cetuximab, or panitumumab on human colorectal cancer xenografts", Oncology Reports, vol. 33, No. 5, May 2015, XP002792830, pp. 2135-2142.
Zhuang, H., et al., "Efficacy and immune mechanisms of Cetuximab for the treatment of metastatic colorectal cancer", Clinical Oncology and Cancer Research. Dec. 24, 2011, vol. 8, No. 4, XP019993879, pp. 207-214.
Yokogawa, T., et al., "TAS-114 Enhances S-1 Activity in Vivo When Used in Combination", European Journal of Cancer, vol. 48, No. Suppl. 6, Nov. 2012, XP002792831, p. 22.
Kobayakawa, M., et al., "Tegafur/gimeracil/oteracil (S-1) approved for the treatment of advanced gastric cancer in adults when given in combination with cisplatin: a review comparing it with other fluoropyrimidine-based therapies", OncoTargets and Therapy, 2011, vol. 4, XP002792832, pp. 193-201.
Fukushima, M., et al., "Structure and Activity of Specific Inhibitors of Thymidine Phosphorylase to Potentiate the Function of Antitumor 2'-Deoxyribonucleosides", Biochemical Pharmacology, vol. 59 No. 10, May 15, 2000, pp. 1227-1236.
Hoff, PM., et al., "Phase I safety and pharmacokinetic study of oral TAS-102 once daily for fourteen days in patients with solid tumors", Clin. Cancer Res., 2000, 6, 4552S-4553S, Suppl.
Dwivedy, S., et al., "Safety and Pharmacokinetics (PK) of an Antitumor/Antiangiogenic Agent, TAS-102: A Phase I Study For Patients (PTS) With Solid Tumors", Proceedings of ASCO, vol. 20, 2001, p. 97a, ab.386.
Thomas, M. B., et al., "A dose-finding, safety and pharmacokinetics study of TAS-102, an antitumor/antiangiogenic agent given orally on a once-daily schedule for five days every three weeks in patients with solid tumors", Proceedings of the American Association for Cancer Research Annual Meeting, Mar. 2002, vol. 43, p. 554. ab. 2754.
Tetsuhiko, S., PhD., "Preclinical and Clinical Practice of S-1 in Japan", Fluoropyrimidines in Cancer Therapy, 2004, pp. 285-302.
Emura, T., et al., "An optimal dosing schedule fora novel combination antimetabolite, TAS-102, based on its intracellular metabolism and its incorporation into DNA", International Journal of Molecular Medicine, Feb. 2004, vol. 13 No. 2, pp. 249-255.
Taiwanese Office Action and Search Report dated Feb. 5, 2020, in Patent Application No. 106100533, 9 pages (with unedited computer generated English translation)
Lee, M. S. and Kopetz, S., "Novel Therapies in Development for Metastatic Colorectal Cancer", Gastrointestinal Cancer Research, Sep. 2015, Supplement 1:S2-S7.
International Search Report dated Mar. 14, 2017, in PCT/JP2017/000266, filed Jan. 6, 2017.
Overman, M.J. et al., "Phase 1 study of TAS-102 administered once daily on a 5-day-per-week schedule in patients with solid tumors", Investigational New Drugs, vol. 26, Jun. 5, 2008, pp. 445-454.
Yoshino, T. et al., "TAS-102 monotherapy for pretreated metastatic colorectal cancer: a double-blind, randomised, placebo-controlled phase 2 trial", Lancet Oncology, vol. 13, Oct. 2012, pp. 993-1001.
Koehler, S.E. et al., "Small Interfering RNA-Mediated Suppression of dUTPase Sensitizes Cancer Cell Lines to Thymidylate Synthase Inhibition", Molecular Pharmacology, vol. 66, No. 3, 2004, pp. 620-626.
Pardoll, D.M., "The blockade of immune checkpoints in cancer immunotherapy", Nature Reviews Cancer, vol. 12, Apr. 2012, pp. 252-264.
Topalian, S.L. et al., "Safety, Activity, and Immune Correlates of Anti-PD-1 Antibody in Cancer", The New England Journal of Medicine, vol. 366, No. 26, Jun. 28, 2012, pp. 2443-2454.
Lesterhuis, W.J. et al., "Synergistic Effect of CTLA-4 Blockade and Cancer Chemotherapy in the Induction of Anti-Tumor Immunity", PLOS One, vol. 8, No. 4, Apr. 2013, pp. 1-8.
Parra, K. et al., "Abstract 2987: Evaluation of CTLA-4 blockage with sequential metronomic chemotherapy for the treatment of preclinical breast cancer", Cancer Research, vol. 74, No. 19 Supplement, Oct. 2014, 4 pages.
Yang, L-L. et al., "Recent advances of immunotherapy in lung cancer: anti-programmed cell death-1/programmed death ligand-1 antibodies", Lung Cancer Management, vol. 3, No. 2, 2014, pp. 175-190.
Office Action dated Jul. 24, 2020 in corresponding Russian Patent Application No. 2018128796 (with English translation), 15 pages.
Kharkevich D.A., "Farmakologiya", Uchebnik, 2010,10$^{th}$ ed., (pp. 72-82), 13 pages, No English translation.
A.I. Vengerovskiy, "Pharmacological incompatibility", Bulletin of Siberian Medicine, 2003, 3, pp. 49-56, No English translation.
Office Action dated Aug. 25, 2020 in corresponding Japanese Patent Application No. 2017-5604152 (with English Translation), 8 pages.
Office Action dated Apr. 8, 2020 in corresponding Russian Patent Application No. 2018128796 (with English Translation), 17 pages.
European Office Action dated Jun. 30, 2020 in European Patent Application No. 17736021.1, 11 pages
Extended European Search Report dated Jul. 2, 2020 in European Patent Application No. 20166270.7, 13 pages.
Thibault Voron, et al., "VEGF-A modulates expression of inhibitory checkpoints on CD8+ T cells in tumors," The Journal of Experimental Medicine, vol. 212, No. 2, XP055683411, 2015, pp. 139-148.
Yasir Y. Elamin, et al., "Immune Effects of Bevacizumab: Killing Two Birds with One Stone," Cancer Microenvironment, vol. 8, XP55708357, 2015, pp. 15-21.
T, Wakasa, et al., "68 Poster TAS-114 in Combination, with Capecitabine-based Chemotherapy May Represent a Novel Therapeutic Strategy," European Journal of Cancer, vol. 48, Supplement 6, Retrieved from the internet: [URL: https://www.sciencedirect.com/journal/european-journal-of-cancer/vol/48/suppl/S6?page=1], XP55708570, Nov. 7, 2012, pp. 22-23.
Office Action dated Oct. 30, 2020 in corresponding New Zealand Patent Application No. 744099, 9 pages.
Utsugi T., "New Challenges and Inspired Answers for Anticancer Drug Discovery and Development", Japanese Journal of Clinical Oncology. 43(10):945-53.
Suzuki et al., "Resolving Question! Q & A of Drugs of Concern Ninth (Completed) Composition of tegafur, gimeracil, and oteracil potassium", Chozai to joho(Rx info), 2015, vol. 21, No. 14, pp. 1979-1989 (with partial English Translation).
Office Action dated Jul. 13, 2021 in Japanese Patent Application No. 2020-110349, (with English Translation).

* cited by examiner

[Fig. 1]
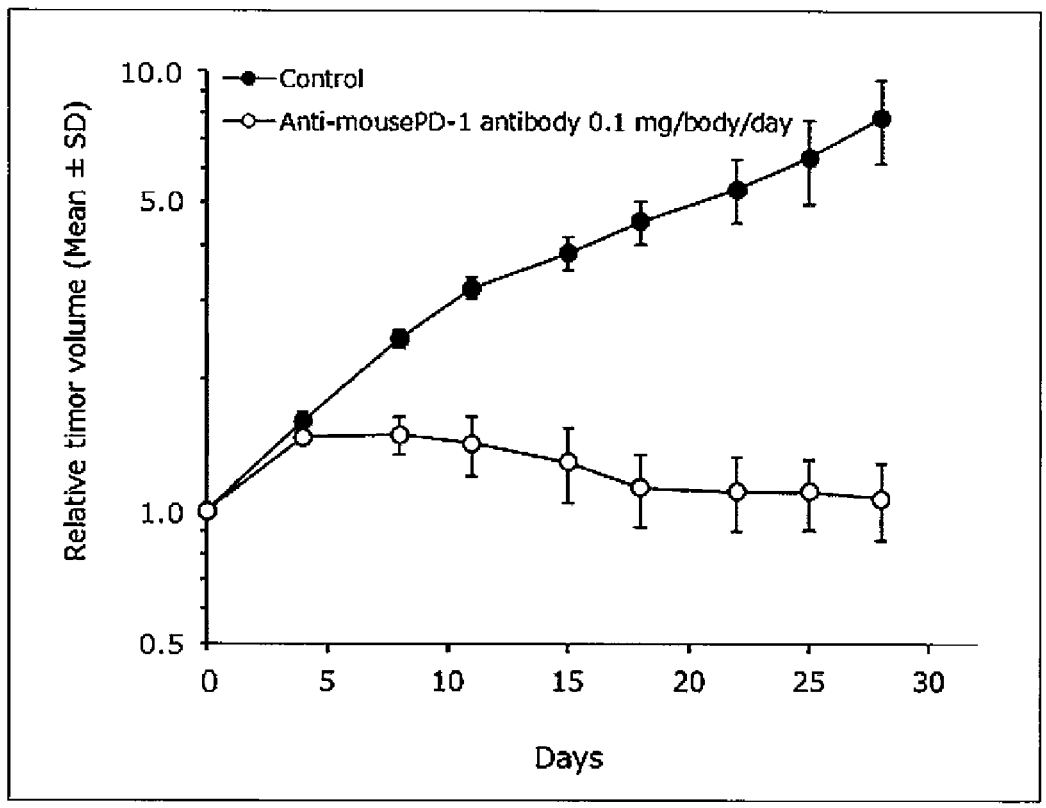
[Fig. 2]
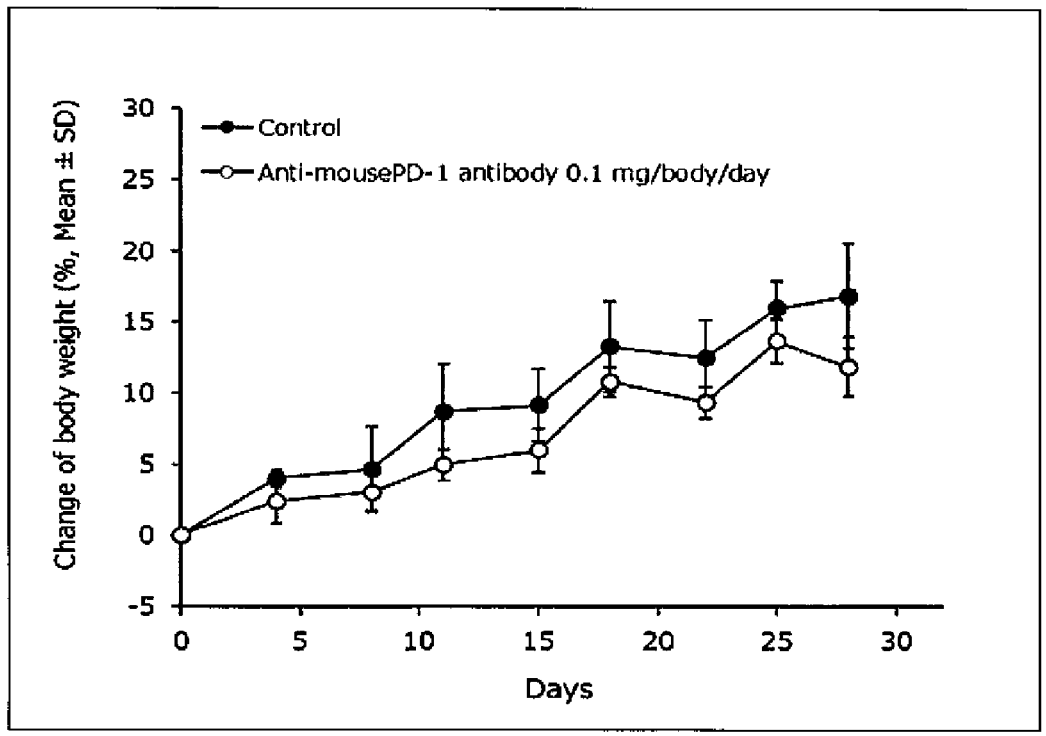

[Fig. 3]
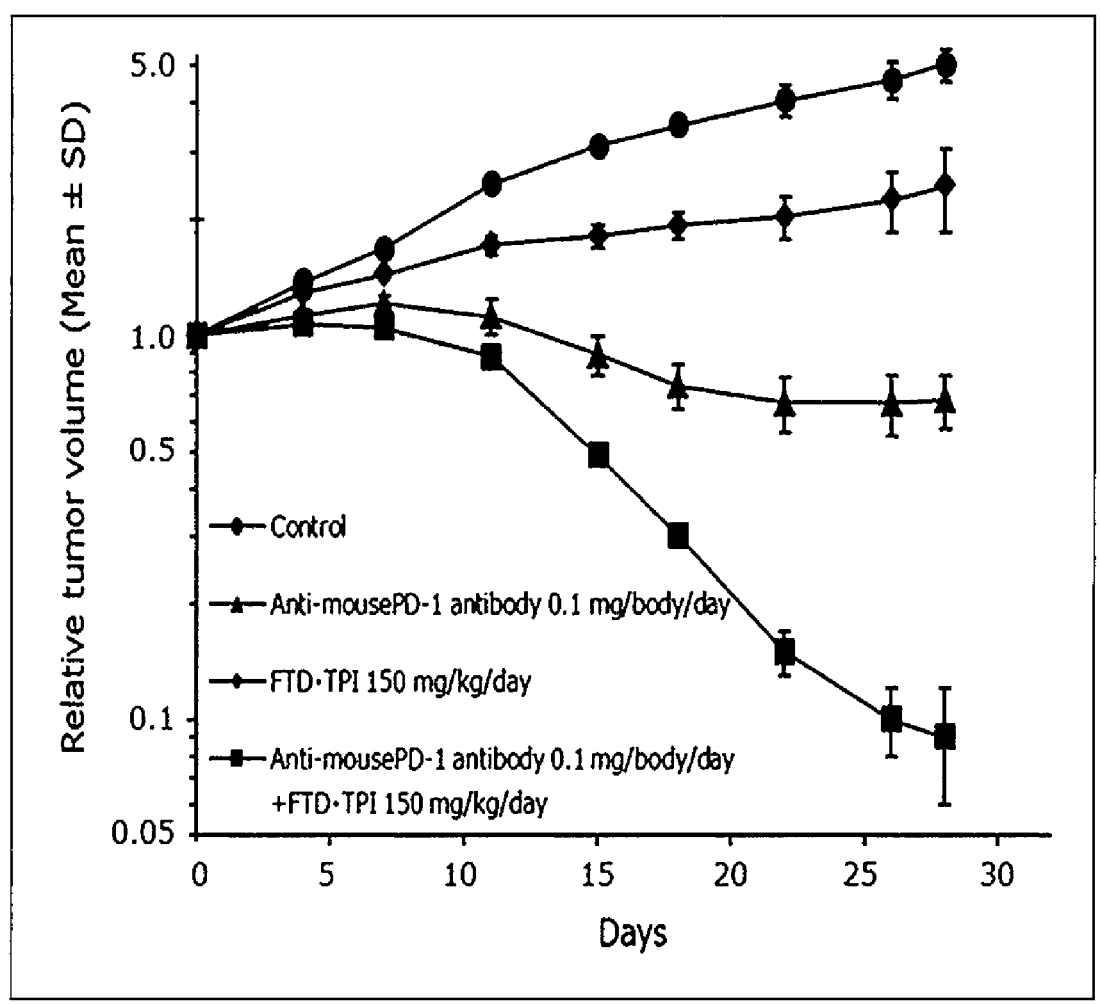

[Fig. 4]
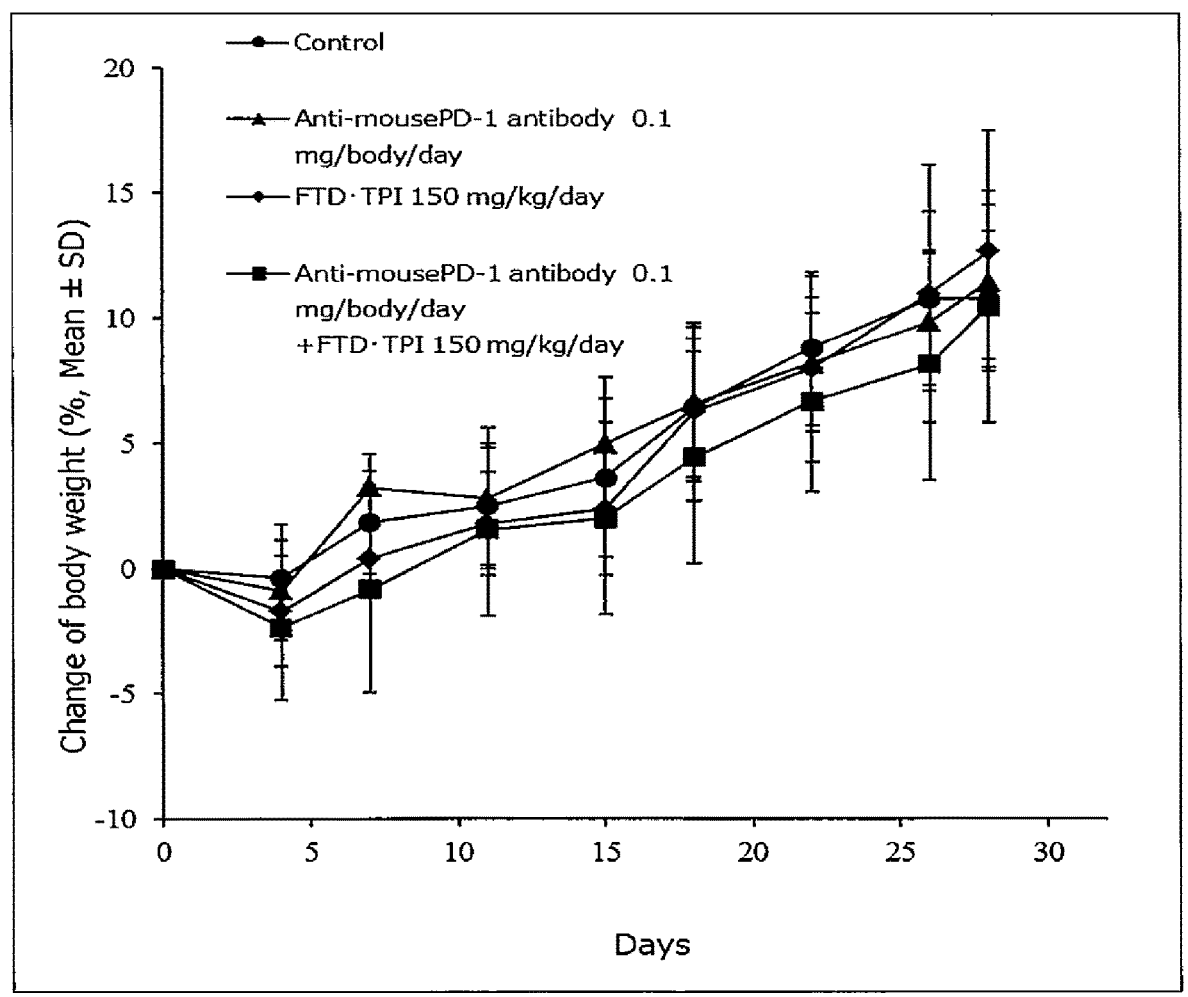

[Fig. 5]
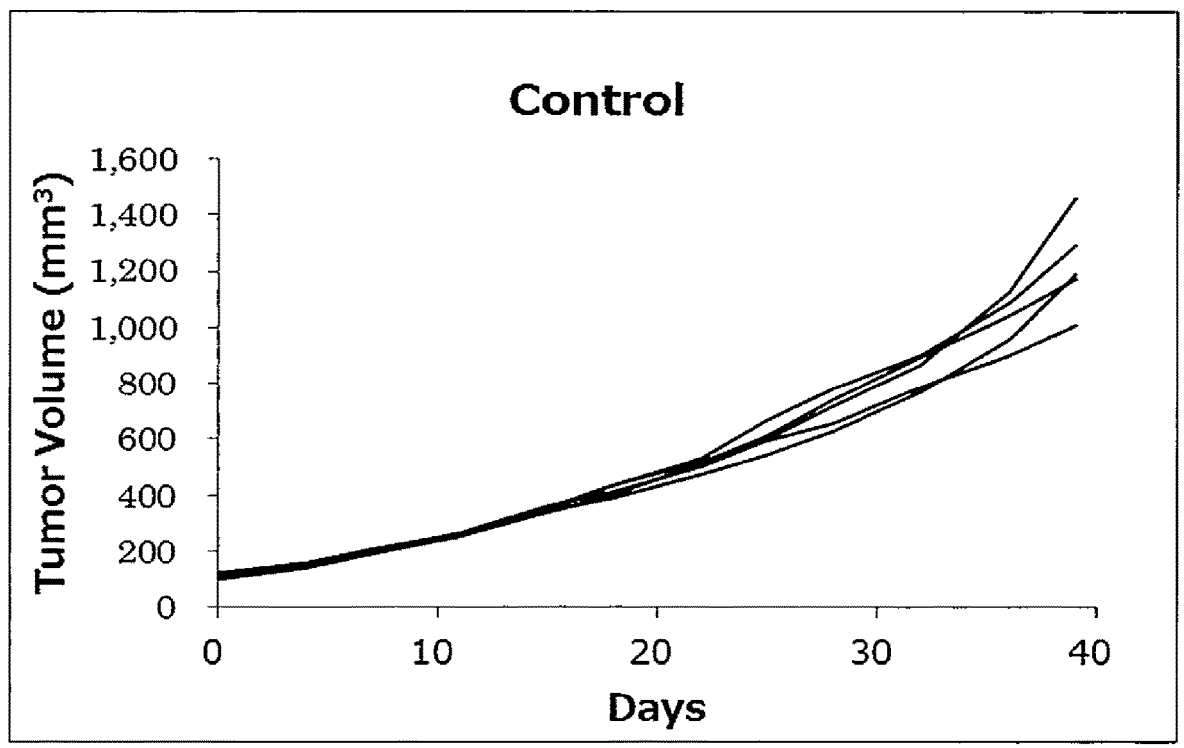
[Fig. 6]
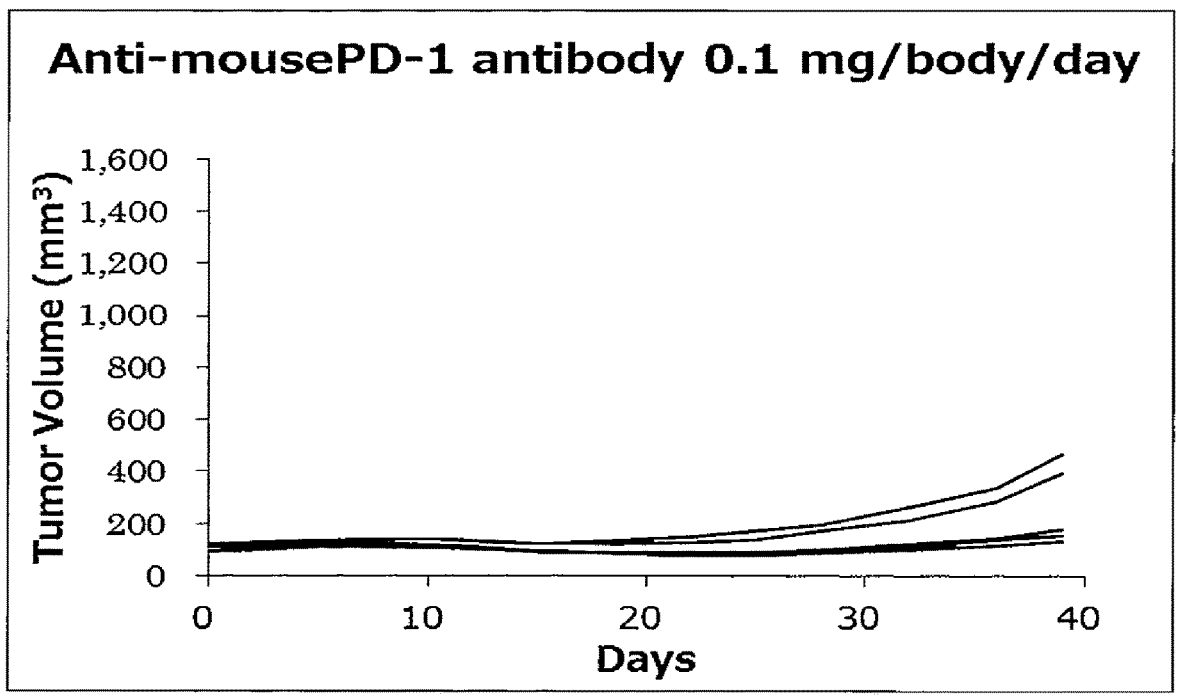

[Fig. 7]
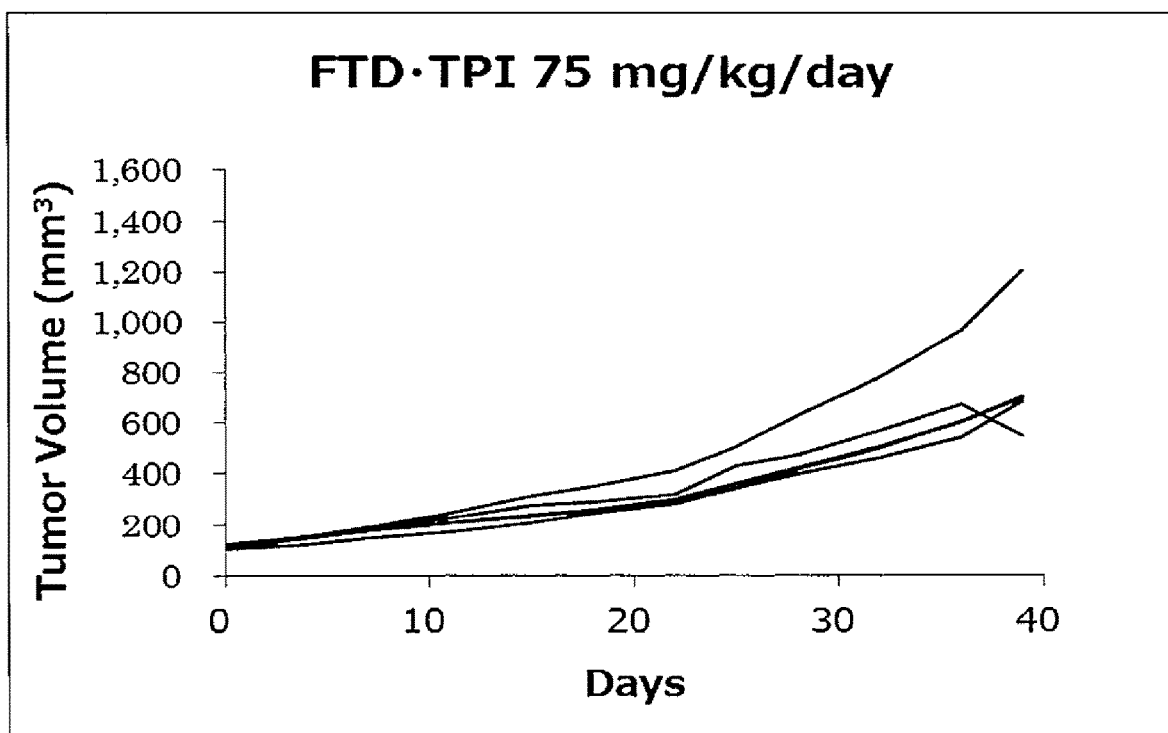

[Fig. 8]
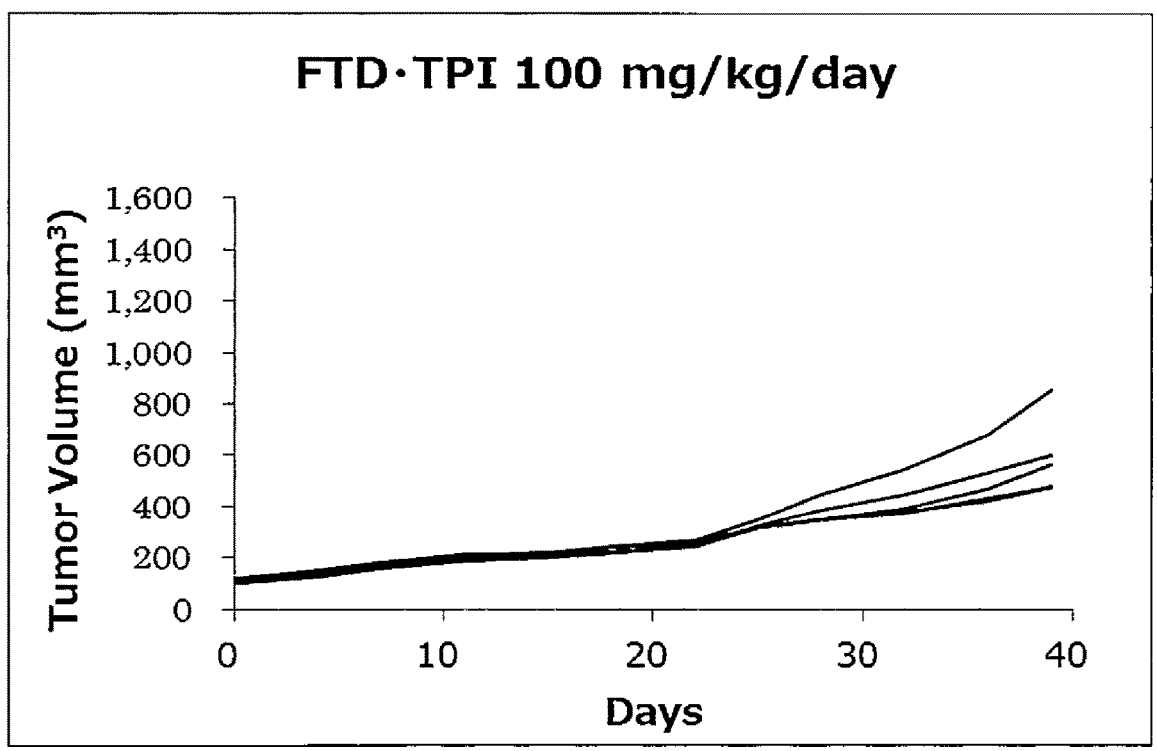
[Fig. 9]
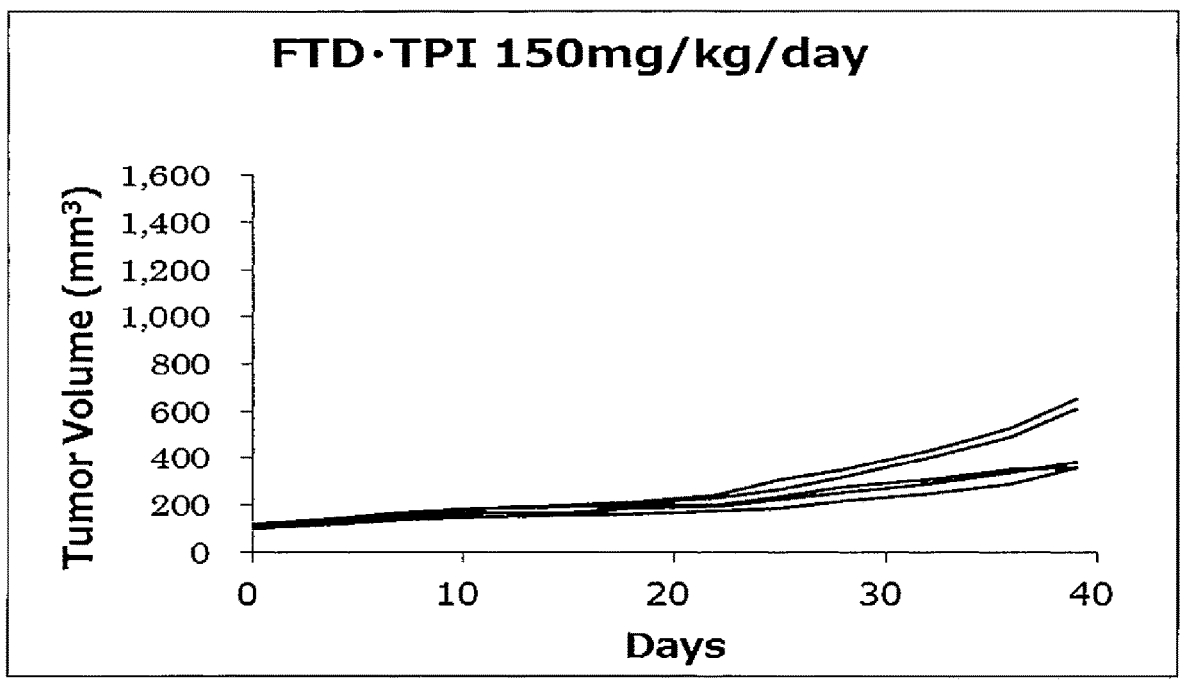

[Fig. 10]
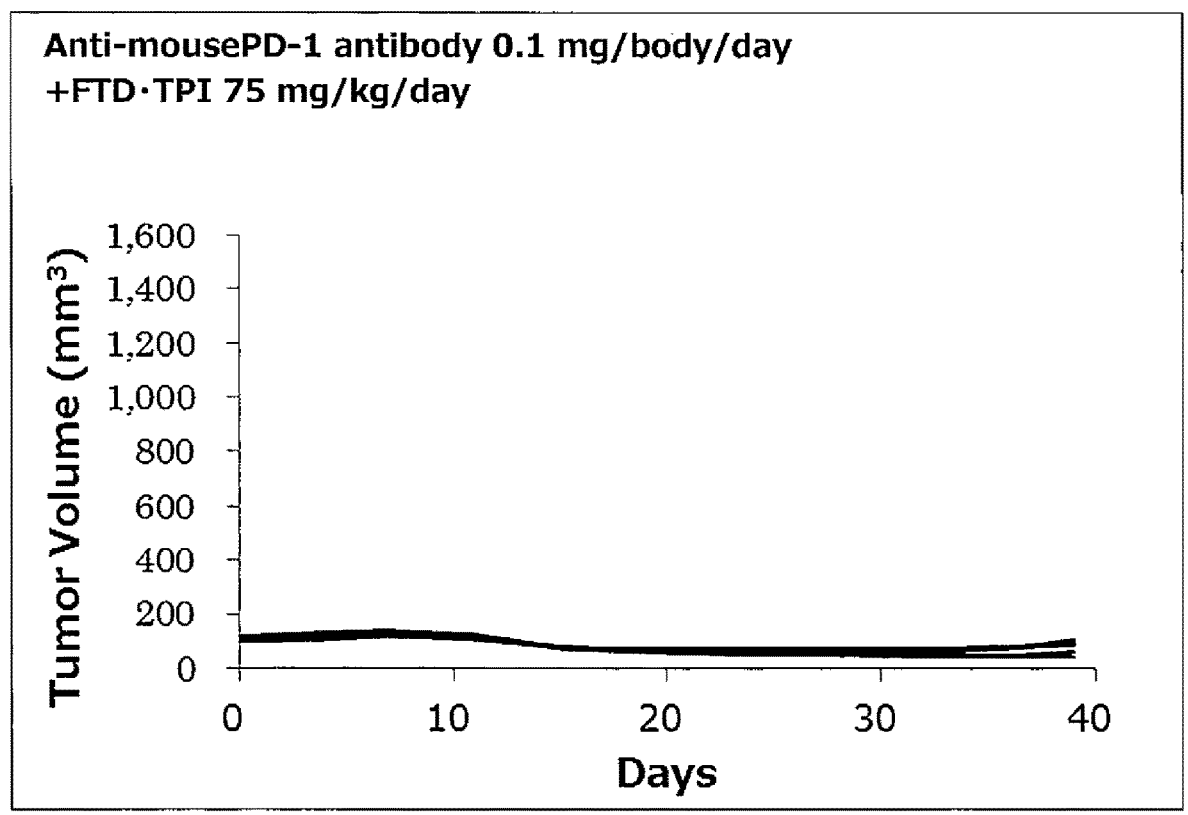

[Fig. 11]
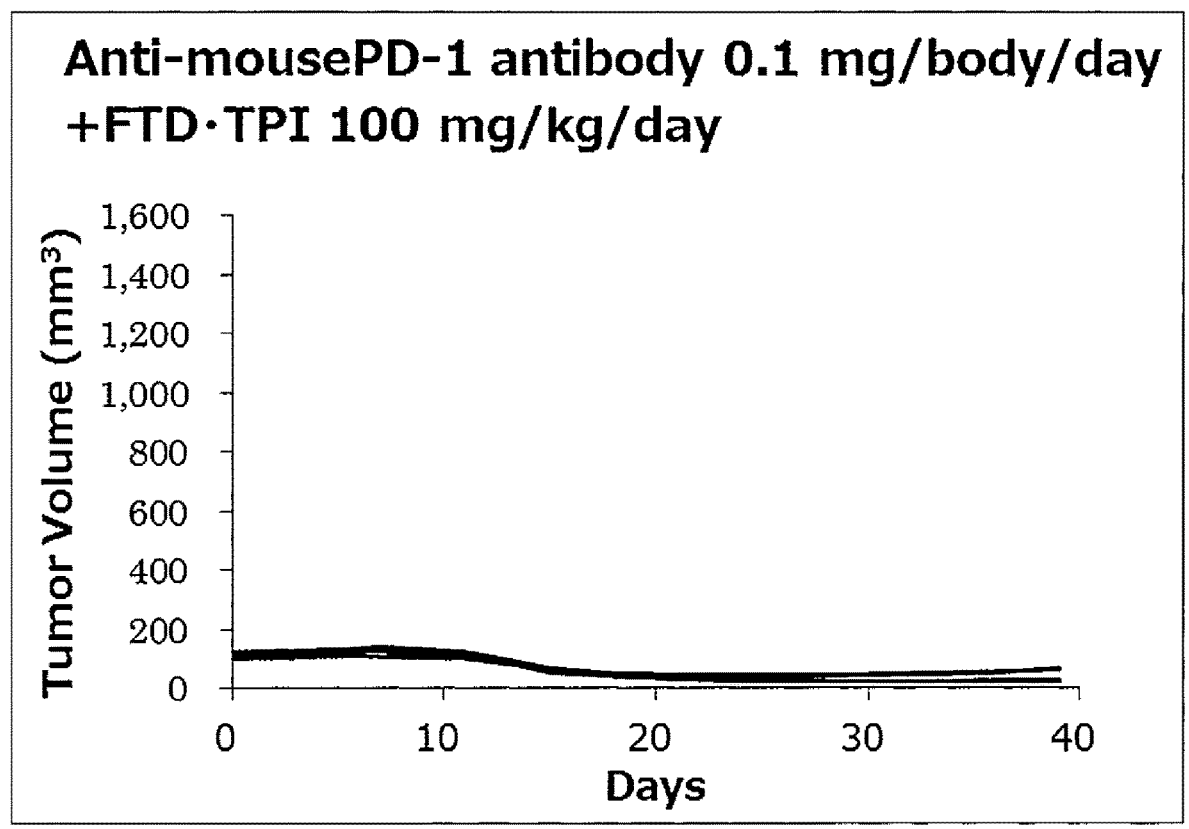

[Fig. 12]
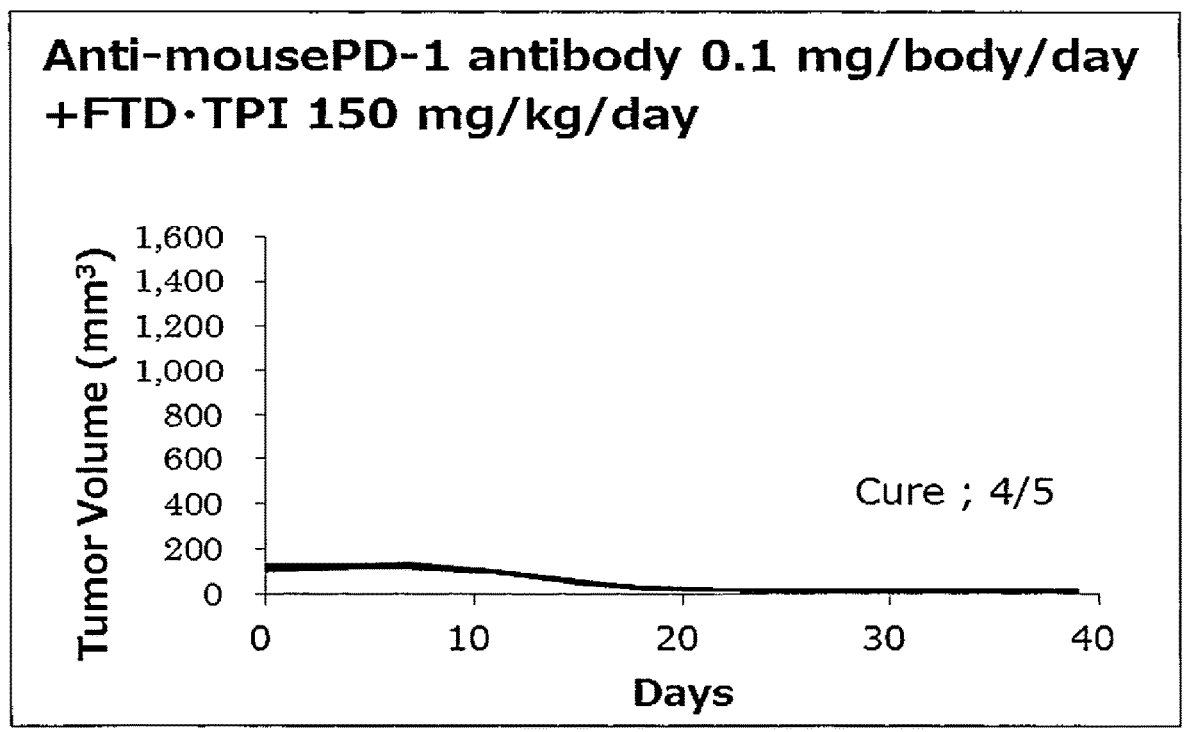

[Fig. 13]
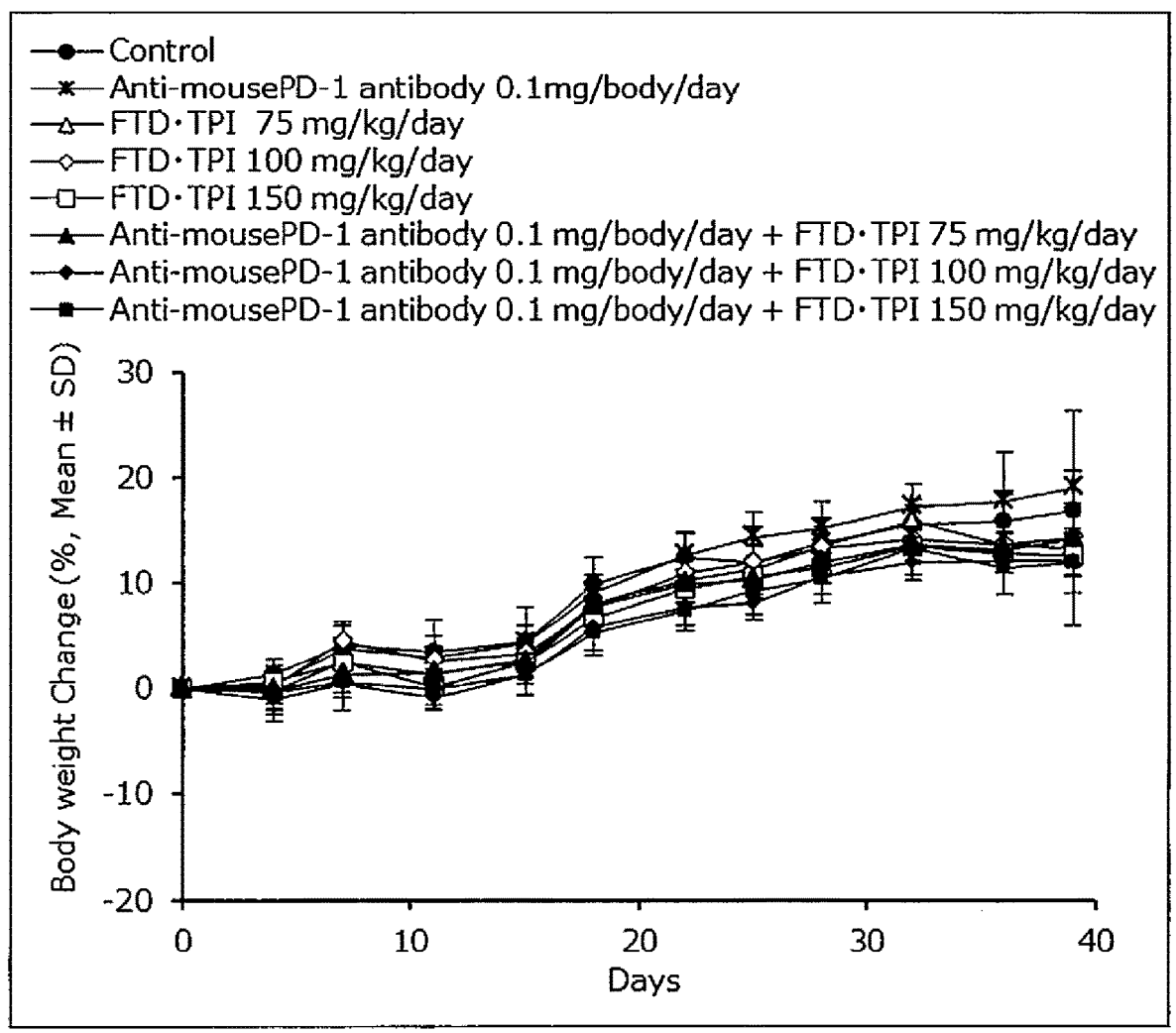

[Fig. 14]
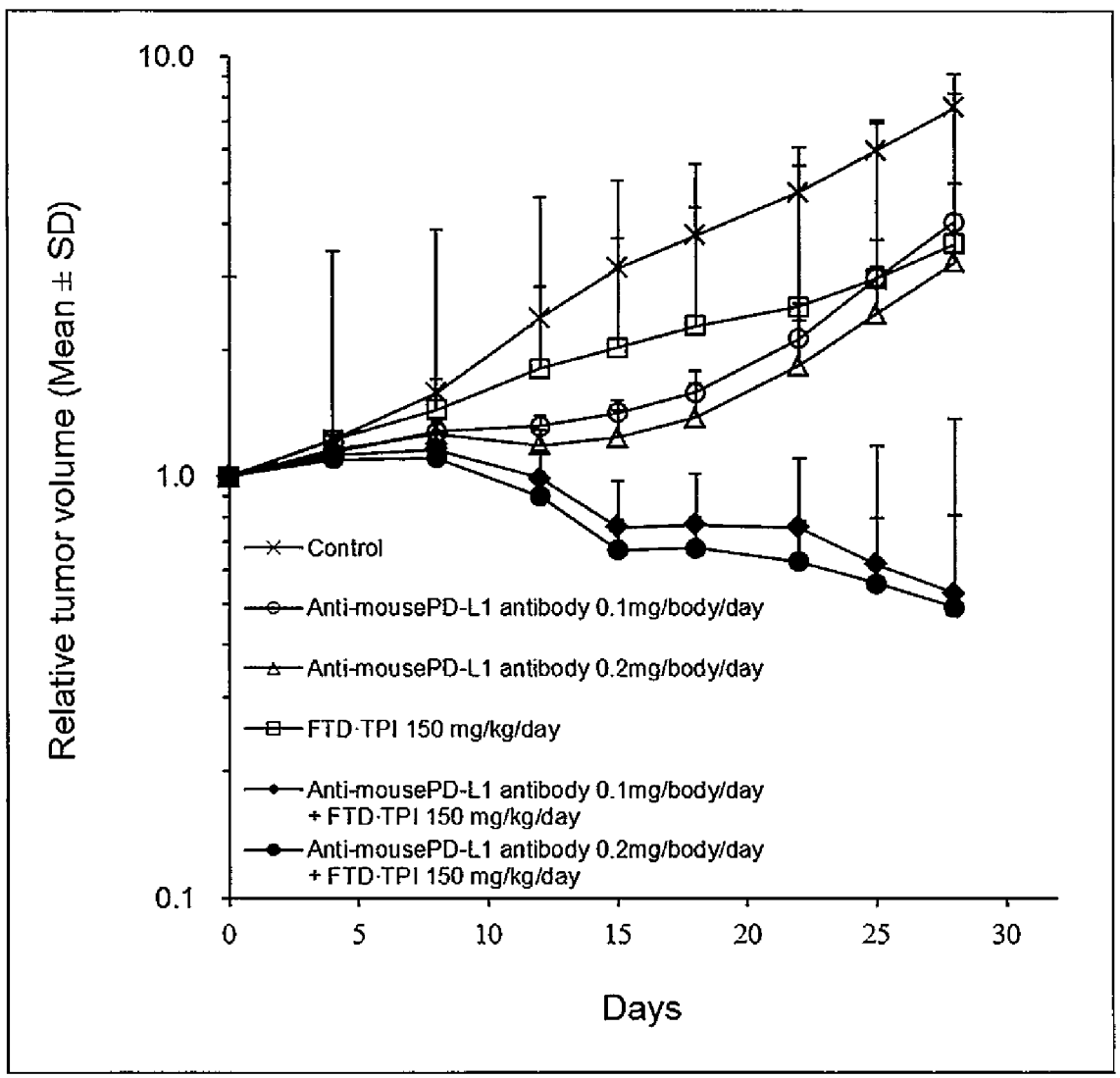

[Fig. 15]
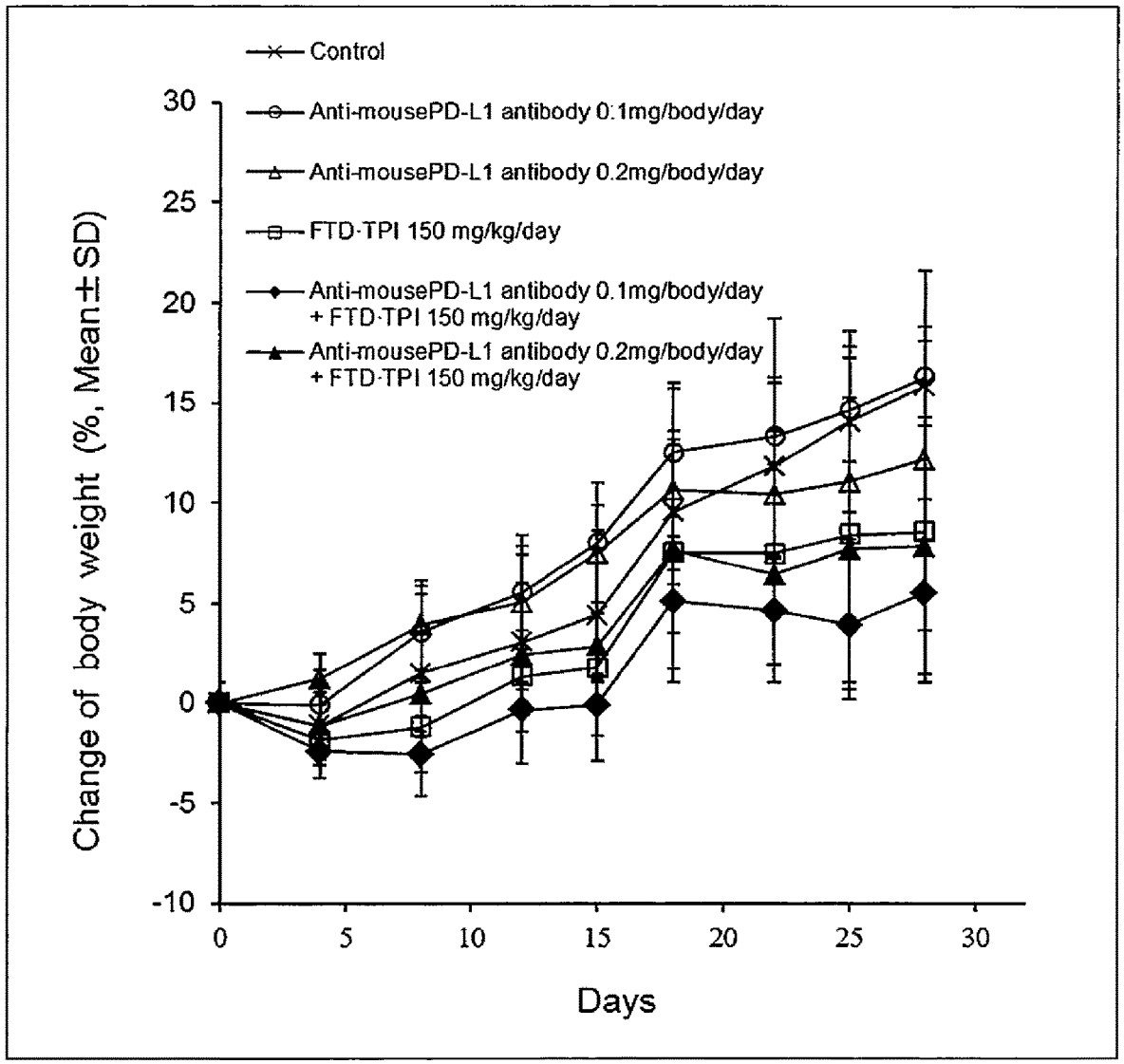

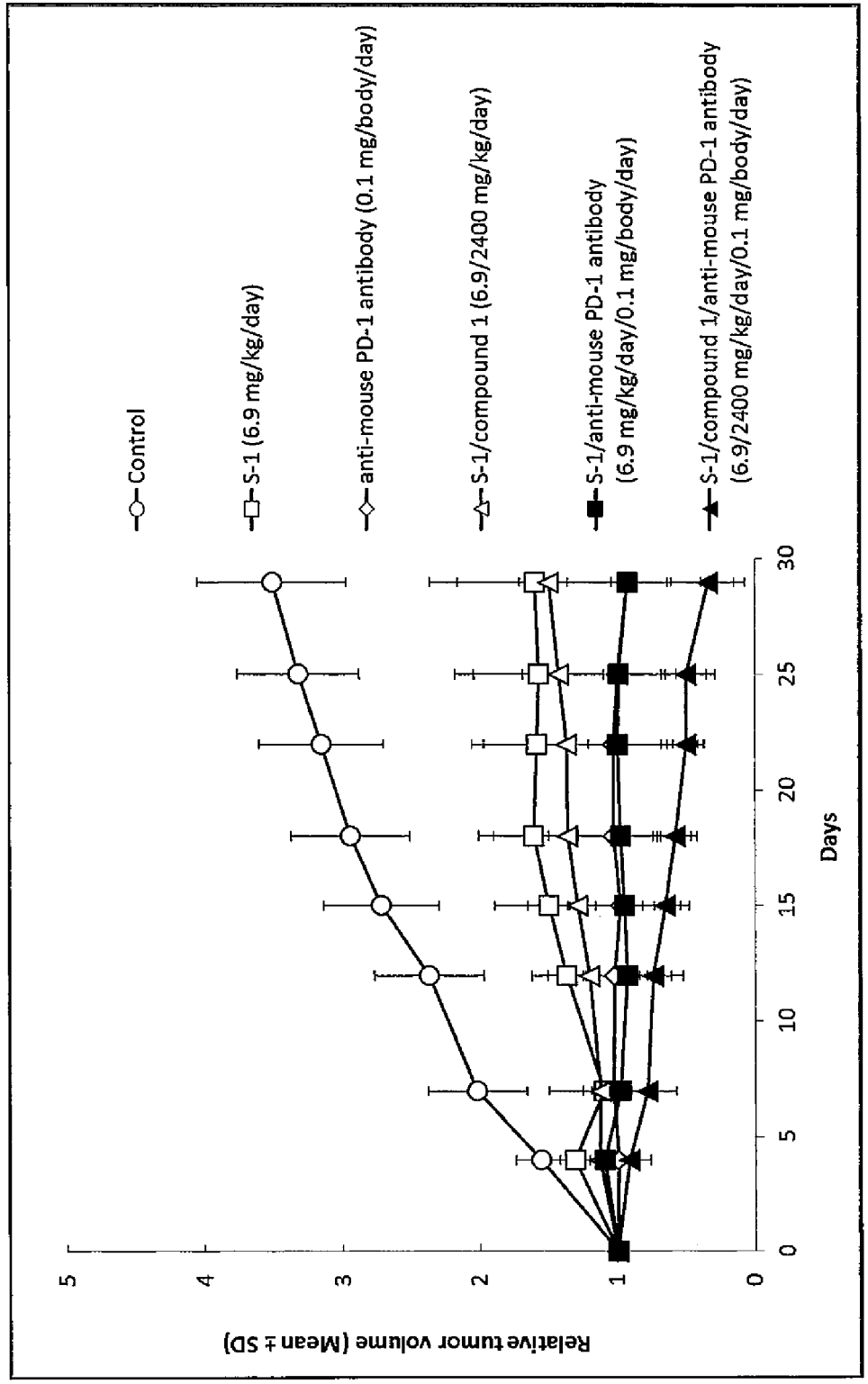
[Fig. 16]

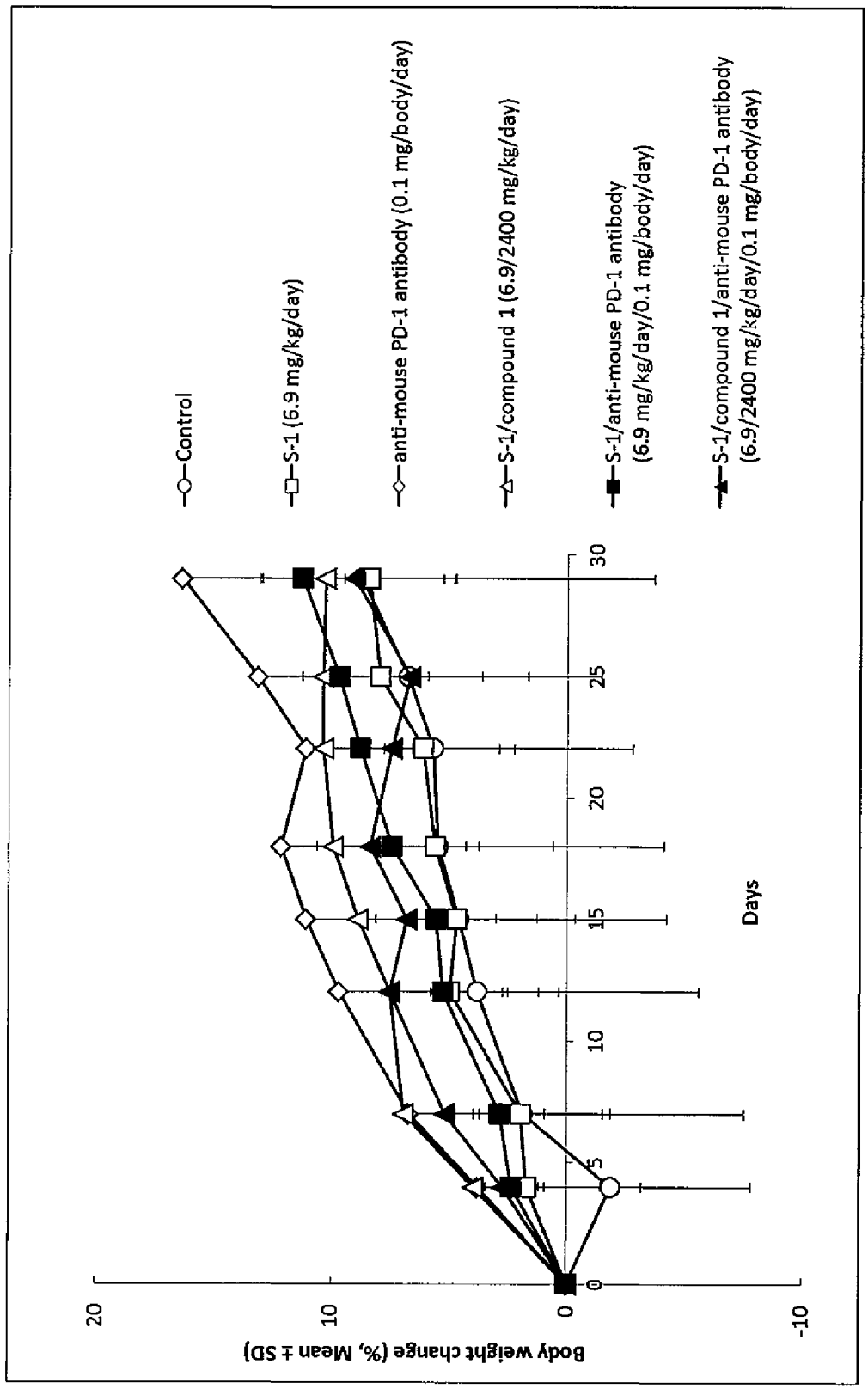
[Fig. 17]

ANTI-TUMOR AGENT CONTAINING IMMUNOMODULATOR, AND ANTITUMOR EFFECT POTENTIATOR

FIELD OF THE INVENTION

The present invention relates to an antitumor agent, an antitumor effect potentiator, and a kit preparation, containing a DNA function inhibitor and an immunomodulator.

BACKGROUND OF THE INVENTION

As a novel therapeutic agent focusing on DNA replication mechanism of cells, a drug containing trifluridine (also known as α,α,α-trifluorothymidine; hereinafter, also referred to as "FTD") and tipiracil hydrochloride (chemical name: 5-chloro-6-[(2-iminopyrrolidine-1-yl)methyl]pyrimidine-2,4(1H,3H)-dione hydrochloride; hereinafter, also referred to as "TPI") is publicly known. FTD exhibits an antitumor effect due to both inhibition of DNA synthesis by thymidylate production-inhibiting activity and inhibition of DNA function by incorporation into DNA. TPI has a thymidine phosphorylase inhibiting activity, and suppresses decomposition of FTD by thymidine phosphorylase in the living body, thereby potentiating the antitumor effect of FTD (Patent Literature 1). Currently, an antitumor agent containing FTD and TPI in a molar ratio of 1:0.5 (hereinafter also referred to as "FTD/TPI combination drug") is under development as a therapeutic agent for a solid cancer. It was approved as a therapeutic agent for metastatic colorectal cancer in Japan and the United States (Non Patent Literatures 1 and 2).

Also, in recent years, deoxyuridine triphosphatase (hereinafter, also referred to as "dUTPase") has been drawing attentions as a novel action mechanism of a cancer treatment focusing on DNA replication mechanism, (Patent Literature 2). dUTPase specifically recognizes deoxyuridine triphosphate (dUTP) only, is one of the enzymes which decompose the same to deoxyuridine monophosphate (dUMP) and pyrophosphoric acid, and also specifically recognizes and decomposes fluorodeoxyuridine triphosphate (FdUTP) such as 5-fluorouracil (hereinafter, also referred to as "5-FU") metabolized from a fluorinated pyrimidine antimetabolite. It is known that when a fluorinated pyrimidine antimetabolite and a dUTPase inhibitor act simultaneously on cells, a dUTP level and an FdUTP level in cells increase and consequently the incorporation of FdUTP into DNA profoundly increases, causing inhibition of DNA function (Patent Literature 3).

Conventionally, 5-FU and derivatives thereof widely used in a clinical practice are phosphorylated in the body to form fluorodeoxyuridine monophosphate (FdUMP), suppress thymidylate synthesis, and inhibit DNA synthesis. Further, 5-FU and derivatives thereof are metabolized into fluorouridine triphosphate (FUTP) in the cell, and incorporated into RNA to cause inhibition of RNA function. FdUMP produced in the body is known to be incorporated into DNA as FdUTP, but an amount thereof is too small to cause the inhibition of DNA function (Non Patent Literature 3). Thus, 5-FU and derivatives thereof are drugs exhibiting an antitumor effect via inhibition of DNA synthesis and inhibition of RNA function, and are not themselves drugs exhibiting an antitumor effect via inhibition of DNA function, thus being different from the above FTD/TPI combination drug, and also from the drug containing both a dUTPase inhibitor and a fluorinated pyrimidine antimetabolite.

On the other hand, currently, development of cancer immunotherapy has been advanced as one of the new methodology of cancer therapy.

Activation of adaptive immune response starts from association of an antigen peptide-MHC complex with a T cell receptor (TCR). The association is further regulated by costimulation or coinhibition by an association between B7 family that is a costimulatory molecule and CD28 family that is a receptor thereof. Specifically, in order to activate T cells in an antigen-specific manner, two characteristic signaling events are required, and T cells receiving only antigen stimulation without receiving costimulation from the B7 family becomes silent by anergy, leading to induce immune tolerance.

Cancer cells suppress activation of antigen-specific T cells using this mechanism, thereby escaping from the immune surveillance and maintaining growth. Therefore, it is considered to be effective for cancer treatment to induce an antitumor immune response in the living body of a cancer patient by enhancing costimulation and blocking coinhibition, and to control immune escape of tumor. Various cancer immunotherapies targeting costimulatory molecule (stimulatory costimulatory molecule) or coinhibitory molecule (inhibitory costimulatory molecule) has been proposed (Non Patent Literature 4). For example, nivolumab (human IgG4 monoclonal antibody on human PD-1) has been used in treatment of, for example, malignant melanoma, as an immunomodulator which activates T cells by inhibiting a binding between PD-1 and a ligand thereof (PD-L1 and PD-L2) (Patent Literature 4 and Non Patent Literature 5).

Furthermore, a combination therapy by combination of a cancer immunotherapy with other cancer treatment method (s) has also been studied, and, for example, a combination therapy including a PD-1 binding antagonist and 5-FU has been reported (Patent Literature 5).

However, as described above, fluorinated pyrimidine antimetabolites such as 5-FU are not such drugs as exhibiting an antitumor effect via inhibition of DNA function. Thus, there has been so far no attempt for the combination therapy between a DNA function inhibitor and an immunomodulator such as anti-PD-1 antibody.

CITATION LIST

Patent Literatures

Patent Literature 1: WO 96/30346
Patent Literature 2: WO 2009/147843
Patent Literature 3: WO 2011/065541
Patent Literature 4: WO 2004/004771
Patent Literature 5: WO 2013/181452

Non Patent Literatures

Non Patent Literature 1: Invest New Drugs. 2008; 26(5): 445-54.
Non Patent Literature 2: Lancet Oncol. 2012; 13(10): 993-1001.
Non Patent Literature 3: Mol Pharmacol. 2004; 66(3): 620-6.
Non Patent Literature 4: Nat Rev Cancer. 2012; 12(4): 252-64.

Non Patent Literature 5: N Engl J Med. 2012; 366(26): 2443-54.

SUMMARY OF THE INVENTION

Problems to be Solved by the Invention

An object of the present invention is to provide a novel cancer treatment method with reduced side effects, while showing remarkably excellent antitumor effect.

Means for Solving the Problem

The present inventor has studied an antitumor effect by using
a drug containing FTD which is a DNA function inhibitor, or a drug containing both a dUTPase inhibitor and a fluorinated pyrimidine antimetabolite, and
an anti-PD-1 antibody or an anti-PD-L1 antibody which is an immunomodulator, in combination, and consequently found that an antitumor effect is further remarkably potentiated without causing serious side effects, as compared to the case of using either of these drugs.

Thus, the present invention provides the following inventions [1] to [81]:
[1] An antitumor agent containing administering a DNA function inhibitor and an immunomodulator in combination.
[2] The antitumor agent according to [1], wherein the DNA function inhibitor is a drug containing trifluridine, or a drug containing a deoxyuridine triphosphatase inhibitor and a fluorinated pyrimidine antimetabolite.
[3] The antitumor agent according to [1] or [2], where the DNA function inhibitor is a combination drug containing trifluridine and tipiracil hydrochloride in a molar ratio of 1:0.5.
[4] The antitumor agent according to [1] or [2], wherein the DNA function inhibitor is a drug containing (R)-N-(1-(3-(cyclopentyloxy)phenyl)ethyl)-3-((2,4-dioxo-3,4-dihydro-pyrimidin-1(2H)-yl)methoxy)propane-1-sulfonamide or a pharmaceutically acceptable salt thereof, and a fluorinated pyrimidine antimetabolite.
[5] The antitumor agent according to [4], wherein the fluorinated pyrimidine antimetabolite is a combination drug containing tegafur, gimeracil, and oteracil potassium in a molar ratio of 1:0.4:1, or capecitabine.
[6] The antitumor agent according to any one of [1] to [5], where the immunomodulator is a PD-1 pathway antagonist, an ICOS pathway antagonist, a CTLA-4 pathway antagonist, a CD28 pathway antagonist, or a combination thereof.
[7] The antitumor agent according to [6], where the PD-1 pathway antagonist is an anti-PD-1 antibody, an anti-PD-L1 antibody, an anti-PD-L2 antibody, or a combination thereof.
[8] The antitumor agent according to [7], wherein the anti-PD-1 antibody is nivolumab or pembrolizumab, and the anti-PD-L1 antibody is atezolizumab, durvalumab, or avelumab.
[9] The antitumor agent according to [6], where the CTLA-4 pathway antagonist is an anti-CTLA-4 antibody.
[10] The antitumor agent according to [9], where the anti-CTLA-4 antibody is ipilimumab or tremelimumab.
[11] The antitumor agent according to any one of [1] to [3] and [6] to [10], where the dose per day of trifluridine on the administration date is 50 to 115% of the recommended dose when administered alone.
[12] The antitumor agent according to any one of [1] to [3] and [6] to [10], where the dose per day of trifluridine on the administration date is 35 to 80 mg/m²/day.
[13] The antitumor agent according to any one of [1] to [12], where the cancer to be targeted is gastrointestinal cancer, lung cancer, or breast cancer.
[14] The antitumor agent according to any one of [1] to [13], where the cancer to be targeted is large bowel cancer.
[15] An antitumor effect potentiator containing a DNA function inhibitor for potentiating an antitumor effect of an immunomodulator.
[16] An antitumor effect potentiator containing an immunomodulator for potentiating an antitumor effect of a DNA function inhibitor.
[17] An antitumor agent containing a DNA function inhibitor for treating a cancer patient administered with an immunomodulator.
[18] An antitumor agent containing an immunomodulator for treating a cancer patient administered with a DNA function inhibitor.
[19] An antitumor agent containing a DNA function inhibitor, which is used in combination with an immunomodulator.
[20] An antitumor agent containing an immunomodulator, which is used in combination with a DNA function inhibitor.
[21] A kit preparation containing an antitumor agent containing a DNA function inhibitor and an instruction for use, the instruction for use describing that a DNA function inhibitor and an immunomodulator are administered to a cancer patient in combination.
[22] Use of a DNA function inhibitor and an immunomodulator for producing an antitumor agent.
[23] The use according to [22], wherein the DNA function inhibitor is a drug containing trifluridine, or a drug containing a deoxyuridine triphosphatase inhibitor and a fluorinated pyrimidine antimetabolite.
[24] The use according to [22] or [23], wherein the DNA function inhibitor is a combination drug containing trifluridine and tipiracil hydrochloride in a molar ratio of 1:0.5.
[25] The use according to [22] or [23], wherein the DNA function inhibitor is a drug containing (R)-N-(1-(3-(cyclopentyloxy)phenyl)ethyl)-3-((2,4-dioxo-3,4-dihydropyrimidin-1(2H)-yl)methoxy)propane-1-sulfonamide or a pharmaceutically acceptable salt thereof, and a fluorinated pyrimidine antimetabolite.
[26] The use according to [25], wherein the fluorinated pyrimidine antimetabolite is a combination drug containing tegafur, gimeracil, and oteracil potassium in a molar ratio of 1:0.4:1, or capecitabine.
[27] The use according to any of [22] to [26], wherein the immunomodulator is a PD-1 pathway antagonist, an ICOS pathway agonist, a CTLA-4 pathway antagonist, a CD28 pathway agonist, or a combination thereof.
[28] The use according to [27], wherein the PD-1 pathway antagonist is an anti-PD-1 antibody, an anti-PD-L1 antibody, an anti-PD-L2 antibody, or a combination thereof.
[29] The use according to [28], wherein the anti-PD-1 antibody is nivolumab or pembrolizumab, and the anti-PD-L1 antibody is atezolizumab, durvalumab, or avelumab.
[30] The use according to [27], wherein the CTLA-4 pathway antagonist is an anti-CTLA-4 antibody.
[31] The use according to [30], wherein the anti-CTLA-4 antibody is ipilimumab or tremelimumab.
[32] The use according to any of [22] to [24] and [27] to [31], wherein the dose per day of trifluridine on the administration date is 50 to 115% of the recommended dose when administered alone.

[33] The use according to any of [22] to [24] and [27] to [31], wherein the dose per day of trifluridine on the administration date is 35 to 80 mg/m$^2$/day.
[34] The use according to any of [22] to [33], wherein the cancer to be targeted is gastrointestinal cancer, lung cancer, or breast cancer.
[35] The use according to any of [22] to [34], wherein the cancer to be targeted is large bowel cancer.
[36] Use of a DNA function inhibitor for producing an antitumor effect potentiator for potentiating an antitumor effect of an immunomodulator.
[37] Use of an immunomodulator for producing an antitumor effect potentiator for potentiating an antitumor effect of a DNA function inhibitor.
[38] Use of a DNA function inhibitor for producing an antitumor agent for treating a cancer patient administered with an immunomodulator.
[39] Use of an immunomodulator for producing an antitumor agent for treating a cancer patient administered with a DNA function inhibitor.
[40] Use of a DNA function inhibitor for producing an antitumor agent used in combination with an immunomodulator.
[41] Use of an immunomodulator for producing an antitumor agent used in combination with a DNA function inhibitor.
[42] A combination of a DNA function inhibitor and an immunomodulator for use in treatment of a tumor.
[43] The combination according to [42], wherein the DNA function inhibitor is a drug containing trifluridine, or a drug containing a deoxyuridine triphosphatase inhibitor and a fluorinated pyrimidine antimetabolite.
[44] The combination according to [42] or [43], wherein the DNA function inhibitor is a combination drug containing trifluridine and tipiracil hydrochloride in a molar ratio of 1:0.5.
[45] The combination according to [42] or [43], wherein the DNA function inhibitor is a drug containing (R)-N-(1-(3-(cyclopentyloxy)phenyl)ethyl)-3-((2,4-dioxo-3,4-dihydro-pyrimidin-1(2H)-yl)methoxy)propane-1-sulfonamide or a pharmaceutically acceptable salt thereof, and a fluorinated pyrimidine antimetabolite.
[46] The combination according to [45], wherein the fluorinated pyrimidine antimetabolite is a combination drug containing tegafur, gimeracil and oteracil potassium in a molar ratio of 1:0.4:1, or capecitabine.
[47] The combination according to any of [42] to [46], wherein the immunomodulator is a PD-1 pathway antagonist, an ICOS pathway agonist, a CTLA-4 pathway antagonist, a CD28 pathway agonist, or a combination thereof.
[48] The combination according to [47], wherein the PD-1 pathway antagonist is an anti-PD-1 antibody, an anti-PD-L1 antibody, an anti-PD-L2 antibody, or a combination thereof.
[49] The combination according to [48], wherein the anti-PD-1 antibody is nivolumab or pembrolizumab, and the anti-PD-L1 antibody is atezolizumab, durvalumab, or avelumab.
[50] The combination according to [47], wherein the CTLA-4 pathway antagonist is an anti-CTLA-4 antibody.
[51] The combination according to [50], wherein the anti-CTLA-4 antibody is ipilimumab or tremelimumab.
[52] The combination according to any of [42] to [44] and [47] to [51], wherein the dose per day of trifluridine on the administration date is 50 to 115% of the recommended dose when administered alone.
[53] The combination according to any of [42] to [44] and [47] to [51], wherein the dose per day of trifluridine on the administration date is 35 to 80 mg/m$^2$/day.
[54] The combination according to any of [42] to [53], wherein the cancer to be targeted is gastrointestinal cancer, lung cancer, or breast cancer.
[55] The combination according to any of [42] to [54], wherein the cancer to be targeted is large bowel cancer.
[56] A DNA function inhibitor for use in potentiation of an antitumor effect of an immunomodulator.
[57] An immunomodulator for use in potentiation of an antitumor effect of a DNA function inhibitor.
[58] A DNA function inhibitor for use in treatment of a cancer patient administered with an immunomodulator.
[59] An immunomodulator for use in treatment of a cancer patient administered with a DNA function inhibitor.
[60] A DNA function inhibitor for use in treatment of a tumor used in combination with an immunomodulator.
[61] An immunomodulator for use in treatment of a tumor used in combination with a DNA function inhibitor.
[62] A method for treating a tumor, the method comprising administering effective doses of a DNA function inhibitor and an immunomodulator to a subject in need thereof.
[63] The method according to [62], wherein the DNA function inhibitor is a drug containing trifluridine, or a drug containing a deoxyuridine triphosphatase inhibitor and a fluorinated pyrimidine antimetabolite.
[64] The method according to [62] or [63], wherein the DNA function inhibitor is a combination drug containing trifluridine and tipiracil hydrochloride in a molar ratio of 1:0.5.
[65] The method according to [62] or [63], wherein the DNA function inhibitor is a drug containing (R)-N-(1-(3-(cyclopentyloxy)phenyl)ethyl)-3-((2,4-dioxo-3,4-dihydropyrimidin-1(2H)-yl)methoxy)propane-1-sulfonamide or a pharmaceutically acceptable salt thereof, and a fluorinated pyrimidine antimetabolite.
[66] The method according to [65], wherein the fluorinated pyrimidine antimetabolite is a combination drug containing tegafur, gimeracil, and oteracil potassium in a molar ratio of 1:0.41, or capecitabine.
[67] The method according to any of [62] to [66], wherein the immunomodulator is a PD-1 pathway antagonist, an ICOS pathway agonist, a CTLA-4 pathway antagonist, a CD28 pathway agonist, or a combination thereof.
[68] The method according to [67], wherein the PD-1 pathway antagonist is an anti-PD-1 antibody, an anti-PD-L1 antibody, an anti-PD-L2 antibody, or a combination thereof.
[69] The method according to [68], wherein the anti-PD-1 antibody is nivolumab or pembrolizumab, and the anti-PD-L1 antibody is atezolizumab, durvalumab, or avelumab.
[70] The method according to [67], wherein the CTLA-4 pathway antagonist is an anti-CTLA-4 antibody.
[71] The method according to [70], wherein the anti-CTLA-4 antibody is ipilimumab or tremelimumab.
[72] The method according to any of [62] to [64] and [67] to [71], wherein the dose per day of trifluridine on the administration date is 50 to 115% of the recommended dose when administered alone.
[73] The method according to any of [62] to [64] and [67] to [71], wherein the dose per day of trifluridine on the administration date is 35 to 80 mg/m$^2$/day.
[74] The method according to any of [62] to [73], wherein the cancer to be targeted is gastrointestinal cancer, lung cancer, or breast cancer.
[75] The method according to any of [62] to [74], wherein the cancer to be targeted is large bowel cancer.

[76] A method for potentiating an antitumor effect of an immunomodulator, the method comprising administering an effective dose of a DNA function inhibitor to a subject in need thereof.

[77] A method for potentiating an antitumor effect of a DNA function inhibitor, the method comprising administering an effective dose of an immunomodulator to a subject in need thereof.

[78] A method for treating a cancer patient administered with an immunomodulator, the method comprising administering an effective dose of a DNA function inhibitor to a subject in need thereof.

[79] A method for treating a cancer patient administered with a DNA function inhibitor, the method comprising administering an effective dose of an immunomodulator to a subject in need thereof.

[80] A method for treating a tumor in combination with using an immunomodulator, the method comprising administering an effective dose of a DNA function inhibitor to a subject in need thereof.

[81] A method for treating a tumor in combination with using a DNA function inhibitor, the method comprising administering an effective dose of an immunomodulator to a subject in need thereof.

Effects of the Invention

According to the antitumor agent of the present invention, it is possible to perform cancer treatment exhibiting high antitumor effect (particularly, effect for reducing tumor size and tumor growth rate (life prolongation effect)) while suppressing the onset of side effects. Eventually, it brings long term survival of cancer patients.

BRIEF DESCRIPTION OF DRAWINGS

FIG. 1 illustrates an antitumor effect on mouse large bowel cancer (CMT-93) in an anti-mouse PD-1 antibody single administration group.

FIG. 2 illustrates a weight change of mouse with large bowel cancer (CMT-93) in an anti-mouse PD-1 antibody single administration group.

FIG. 3 illustrates an effect of combinatorial use of an FTD/TPI combination drug and an anti-mouse PD-1 antibody on mouse large bowel cancer (CMT-93).

FIG. 4 illustrates a weight change of mouse with large bowel cancer (CMT-93) in a co-administration group using an FTD/TPI combination drug and an anti-mouse PD-1 antibody in combination.

FIG. 5 illustrates an effect of combinatorial use of an FTD/TPI combination drug and an anti-mouse PD-1 antibody on mouse large bowel cancer (CMT-93); in Control group.

FIG. 6 illustrates an effect of combinatorial use of an FTD/TPI combination drug and an anti-mouse PD-1 antibody on mouse large bowel cancer (CMT-93); in anti-mouse PD-1 antibody 0.1 mg/body/day group.

FIG. 7 illustrates an effect of combinatorial use of an FTD/TPI combination drug and an anti-mouse PD-1 antibody on mouse large bowel cancer (CMT-93); in FTD/TPI 75 mg/kg/day group.

FIG. 8 illustrates an effect of combinatorial use of an FTD/TPI combination drug and an anti-mouse PD-1 antibody on mouse large bowel cancer (CMT-93); in FTD/TPI 100 mg/kg/day group.

FIG. 9 illustrates an effect of combinatorial use of an FTD/TPI combination drug and an anti-mouse PD-1 antibody on mouse large bowel cancer (CMT-93); in FTD/TPI 150 mg/kg/day group.

FIG. 10 illustrates an effect of combinatorial use of an FTD/TPI combination drug and an anti-mouse PD-1 antibody on mouse large bowel cancer (CMT-93); in anti-mouse PD-1 antibody 0.1 mg/body/day+FTD/TPI 75 mg/kg/day group.

FIG. 11 illustrates an effect of combinatorial use of an FTD/TPI combination drug and an anti-mouse PD-1 antibody on mouse large bowel cancer (CMT-93); in anti-mouse PD-1 antibody 0.1 mg/body/day+FTD/TPI 100 mg/kg/day group.

FIG. 12 illustrates an effect of combinatorial use of an FTD/TPI combination drug and an anti-mouse PD-1 antibody on mouse large bowel cancer (CMT-93); in anti-mouse PD-1 antibody 0.1 mg/body/day+FTD/TPI 150 mg/kg/day group.

FIG. 13 illustrates a weight change of mouse with large bowel cancer (CMT-93) in a co-administration group using an FTD/TPI combination drug and an anti-mouse PD-1 antibody in combination.

FIG. 14 illustrates an effect of combinatorial use of an FTD/TPI combination drug and an anti-mouse PD-L1 antibody on mouse large bowel cancer (CMT-93).

FIG. 15 illustrates a weight change of mouse with large bowel cancer (CMT-93) in a co-administration group using an FTD/TPI combination drug and an anti-mouse PD-L1 antibody in combination.

FIG. 16 illustrates an effect of combinatorial use of S-1+Compound 1 and an anti-mouse PD-1 antibody on mouse large bowel cancer (CMT-93).

FIG. 17 illustrates a weight change of mouse with large bowel cancer (CMT-93) in a co-administration group using S-1+Compound 1 and an anti-mouse PD-1 antibody in combination.

DETAILED DESCRIPTION OF THE INVENTION

The present invention relates to an antitumor agent, an antitumor effect potentiator, a kit preparation, for administering a DNA function inhibitor (particularly, an FTD/TPI combination drug) and an immunomodulator (particularly, an anti-PD-1 antibody) in combination, and use of these agents, a method for treating a tumor, and a method for potentiating an antitumor effect.

The DNA function inhibitor in the present invention refers to a drug which increases incorporation of wrong nucleobases into DNA within a tumor cell to cause inhibition of DNA function and thus exhibits an antitumor effect.

Examples of the specific DNA function inhibitor include a drug containing FTD, and a drug containing dUTPase inhibitor and a fluorinated pyrimidine antimetabolite.

Examples of the drug containing FTD in the present invention include a combination drug containing FTD and TPI, and it is preferable to contain FTD and TPI in a molar ratio of 1:0.5. FTD and TPI are each a known compound, and can be synthesized, for example, according to a method described in WO 1996/30346. A combination drug containing FTD and TPI in a molar ratio of 1:0.5 is also publicly known (Non Patent Literatures 1 and 2). In addition, the FTD/TPI combination drug was approved as a therapeutic agent for metastatic colorectal cancer in Japan and the United States, and, as the usage and dosage, 70 mg/m$^2$/day as FTD is orally administered twice a day for 5 consecutive days, followed by rest for 2 days. This is repeated twice, and followed by rest for 14 days. It is defined that the administration is repeated with the above procedure as one course.

The "dUTPase inhibitor" in the "drug containing a dUTPase inhibitor and a fluorinated pyrimidine antimetabolite" of the present invention is not particularly limited as long as a compound has an inhibitory activity of dUTPase. Examples preferably include (R)-N-(1-(3-(cyclopentyloxy)phenyl)ethyl)-3-((2,4-dioxo-3,4-dihydropyrimidin-1(2H)-yl)methoxy)propane-1-sulfonamide represented by the following formula (1) (hereinafter, also referred to as "Compound 1") or a pharmaceutically acceptable salt thereof. Compound 1 includes optical isomers and hydrates.

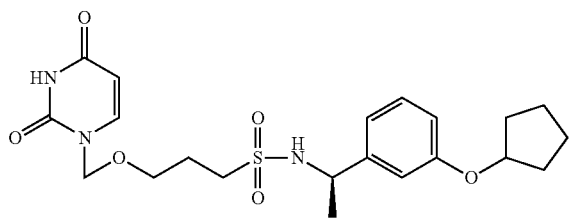

(1)

Compound 1 is a known compound which has a good dUTPase inhibitory activity and can be synthesized by following the method described in, for example, International Publication No. WO2009/147843. Compound 1 is also known to potentiate an antitumor effect of fluorinated pyrimidine antimetabolites such as 5-FU (International Publication No. WO2011/065541).

The "fluorinated pyrimidine antimetabolite" in the "drug containing a dUTPase inhibitor and a fluorinated pyrimidine antimetabolite" of the present invention is not particularly limited as long as it has a fluorinated pyrimidine structure and exhibits an antitumor effect as 5-FU in cells, and includes 5-FU, derivatives thereof and prodrugs thereof. Specifically, examples include 5-FU, tegafur, a combination drug containing tegafur, gimeracil, and oteracil potassium in a molar ratio of 1:0.4:1 (hereinafter, also referred to as "tegafur/gimeracil/oteracil potassium combination drug", "S-1"), a combination drug containing tegafur and uracil in a molar ratio of 1:4 (hereinafter, also referred to as "tegafur/uracil combination drug", "UFT"), capecitabine, doxifluridine, 5-fluoro-2'-deoxyuridine (FdUrd), and carmofur, and 5-FU, a tegafur/gimeracil/oteracil potassium combination drug, a tegafur/uracil combination drug, and capecitabine are preferable, a tegafur/gimeracil/oteracil potassium combination drug and capecitabine are more preferable, and a tegafur/gimeracil/oteracil potassium combination drug is particularly preferable.

The immunomodulator in the present invention has an activity of inducing an antitumor immune response in the living body of a cancer patient and controlling immune escape of tumor.

An example of such substance includes a substance promoting a function of costimulatory molecule (stimulant costimulatory molecule), or a substance promoting a function of coinhibitory molecule (inhibitory costimulatory molecule). Currently, a large number of B7 family and CD28 family are identified, and substances targeting these can be used without being particularly limited, in the present invention. Examples include a PD-1 pathway antagonist, an ICOS pathway antagonist, a CTLA-4 pathway antagonist, a CD28 pathway antagonist, and a BTLA pathway antagonist.

In the present invention, the immunomodulator is preferably a PD-1 pathway antagonist, an ICOS pathway antagonist, a CTLA-4 pathway antagonist, a CD28 pathway antagonist, or a combination thereof, more preferably a PD-1 pathway antagonist or a CTLA-4 pathway antagonist, and from the viewpoint of suppressing side effects, further more preferably a PD-1 pathway antagonist.

The PD-1 pathway antagonist inhibits PD-1 expressed on T cells, or immunoinhibitory signal by PD-L1 or PD-L2 that is a ligand thereof, and is preferably an anti-PD-1 antibody, an anti-PD-L1 antibody, an anti-PD-L2 antibody, a PD-1 extracellular domain, a PD-L1 extracellular domain, a PD-L2 extracellular domain, PD-1-Ig (fusion protein of PD-1 extracellular domain and FC region of Ig), PD-L1-Ig, and PD-L2-Ig, more preferably an anti-PD-1 antibody, an anti-PD-L1 antibody, and an anti-PD-L2 antibody, and more preferably an anti-PD-1 antibody and an anti-PD-L1 antibody. Among them, preferred is an anti-PD-1 antibody.

The CTLA-4 pathway antagonist inhibits CTLA-4 expressed on T cells, or immunoinhibitory signal by B7-1 (CD80) or B7-2 (CD86) that is a ligand thereof, and is preferably an anti-CTLA-4 antibody, a CTLA-4 extracellular domain, CTLA-4-Ig, an anti-B7-1/CD80 antibody, and an anti-B7-2/CD86 antibody, and more preferably, an anti-CTLA-4 antibody and CTLA-4-Ig. Among them, preferred is an anti-CTLA-4 antibody.

These antibodies may be any antibody of a human-derived antibody, a mouse-derived antibody, a rat-derived antibody, a rabbit-derived antibody, a goat-derived antibody, a llama-derived antibody, and a chicken-derived antibody, and may be any of a polyclonal antibody, a monoclonal antibody, and a complete or truncated (for example, F(ab')$_2$, Fab', Fab or Fv fragment) antibody, a chimerized antibody, a humanized antibody or a completely human antibody thereof.

Preferably, the antibody is a humanized antibody or a completely human antibody, and is a monoclonal antibody.

Specific examples of the anti-PD-1 antibody in the present invention include nivolumab or pembrolizumab, and nivolumab is preferable.

Examples of the anti-PD-L1 antibody in the present invention specifically include atezolizumab, durvalumab, and avelumab, and atezolizumab is preferable.

Specific examples of the anti-CTLA-4 antibody in the present invention include ipilimumab or tremelimumab, and ipilimumab is preferable.

Specific examples of the CTLA-4-Ig in the present invention include abatacept.

These antibodies can be produced by a conventionally known antibody preparation method, for example, can be produced by the method of Patent Literature 2.

In addition, the anti-PD-1 antibody as nivolumab or pembrolizumab, the anti PD-L1 antibody as atezolizumab, durvalumab or avelumab, the anti-CTLA-4 antibody as ipilimumab or tremelimumab, and the CTLA-4-Ig as abatacept are already sold or to be sold, and these can be also used.

The dose per day on the administration date of the DNA function inhibitor in the present invention, in the case of the FTD/TPI combination drug (FTD and TPI in a molar ratio of 1:0.5), is preferably 50 to 115% of the recommended dose when the FTD/TPI combination drug is administered alone, more preferably 50 to 100%, more preferably 67 to 100%, and particularly preferably 100%, from the viewpoint of an activity of potentiating an antitumor effect of the immunomodulator by the FTD/TPI combination drug. Specifically, the recommended dose when the FTD/TPI combination drug is administered alone in human is 70 mg/m$^2$/day as FTD that is the dose approved in Japan as described above, thus the dose per day on the administration date of the FTD/TPI combination drug in the present invention is preferably 35 to 80 mg/m$^2$/day, more preferably 35 to 70 mg/m$^2$/day, more preferably 50 to 70 mg/m$^2$/day, and particularly preferably 70 mg/m$^2$/day as FTD.

In addition, when the DNA function inhibitor is a drug containing Compound 1 or a pharmaceutically acceptable salt thereof and the tegafur/gimeracil/oteracil potassium combination drug, the dose per day of Compound 1 on the administration date is preferably 12 to 1,200 mg/m$^2$/day, more preferably 120 to 600 mg/m$^2$/day, and particularly preferably 240 to 480 mg/m$^2$/day. Further, when the dose per day of Compound 1 on the administration date is defined on a patient-specific basis, 20 to 2,000 mg/body/day is preferable, 200 to 1,000 mg/body/day is more preferable, and 400 to 800 mg/body/day is particularly preferable.

Further, the dose per day of the tegafur/gimeracil/oteracil potassium combination drug on the administration date is, as tegafur amount, preferably 10 to 200 mg/m$^2$/day, more preferably 20 to 80 mg/m$^2$/day, and particularly preferably 40 to 72 mg/m$^2$/day.

Furthermore, when the DNA function inhibitor is a drug containing Compound 1 or a pharmaceutically acceptable salt thereof and capecitabine, the dose per day of Compound 1 on the administration date is preferably 12 to 3,000 mg/m$^2$/day, more preferably 240 to 1,200 mg/m$^2$/day, and particularly preferably 480 to 720 mg/m$^2$/day. Additionally, when the dose per day or Compound 1 on the administration date is defined on a patient-specific basis, 20 to 5,000 mg/body/day is preferable, 400 to 2,000 mg/body/day is more preferable, and 800 to 1,200 mg/body/day is particularly preferable.

Further, the dose per day of capecitabine on the administration date is preferably 200 to 3,000 mg/m$^2$/day, more preferably 480 to 1,400 mg/m$^2$/day, and particularly preferably 600 to 900 mg/m$^2$/day.

The dose to a patient can be determined based on the body surface area (BSA) calculated from the patients height and body weight. As a method for calculating a body surface area, a conventional method is appropriately used, depending on, for example, the race, sex, health condition and symptom of the patient, for example, the following calculation formulae 1 to 6, and preferably the following formula 1 or 2(a).

1. The Mosteller formula (See N Engl J Med 1987 Oct. 22; 317 (17): 1098 (letter))

BSA (m$^2$)=([Height (cm)×Weight (kg)]/3600)1/2

2. The DuBois and DuBois formula (See Arch Int Med 1916 17: 863-71; J Olin Anesth. 1992; 4(1): 4-10)

(a) BSA (m$^2$)=0.20247×Height (m)$^{0.725}$×Weight (kg)$^{0.425}$ (b) BSA (m$^2$)=0.007184×Height (cm)$^{0.725}$ ×Weight (kg)$^{0.425}$ 3. The Haycock formula (See The Journal of Pediatrics 1978 93: 1:62-66)

BSA (m$^2$)=0.024265×Height (cm)$^{0.3964}$×Weight (kg)$^{0.5378}$

4. The Gehan and George formula (See Cancer Chemother Rep 1970 54: 225-35) BSA (m$^2$)=0.0235×Height (cm)$^{0.42246}$×Weight (kg)$^{0.51456}$ 5. The Boyd formula (See Minneapolis: university of Minnesota Press, 1935)

BSA (m$^2$)=0.0003207×Height (cm)$^{0.3}$×Weight (gram) $(0.7285-(0.0188 \times ^{Log(gram)})$ 6. The Fujimoto formula (See Nihon Eiseigaku Zasshi, 1968 23(5): 443-450)

BSA (m$^2$)=0.008883×Height (cm)$^{0.664}$×Weight (kg)$^{0.444}$

For example, when the body surface area of a cancer patient of 175 cm in height and 70 kg in weight is calculated using the above calculation formula 1, the body surface area is calculated as [175 (cm)×70 (kg)]/3600)1/2=1.84 (m$^2$). When the dose is 60 mg/m$^2$/day in the patient, the total daily dose is calculated as 1.84×60=111 mg, and set to about 110 mg.

The dose per day of the immunomodulator on the administration date in the present invention is preferably 50 to 100% and more preferably 100% of the recommended dose when the DNA function inhibitor is administered alone, from the viewpoint of an activity of potentiating an antitumor effect of the immunomodulator by the DNA function inhibitor.

Specifically, the recommended dose when nivolumab is administered alone is 2 mg/kg (weight) per once that is the dose approved in Japan, thus the dose per day of nivolumab on the administration date in the present invention is preferably 1 to 2 mg/kg (weight) per once and more preferably 2 mg/kg (weight) per once.

The recommended dose when atezolizumab is administered alone is 1,200 mg per once, which is the dose approved in the US, and thus the dose per day of atezolizumab on the administration date in the present invention is preferably 600 to 1,200 mg per once, and more preferably 1,200 mg per once.

The term "recommended dose" in the present invention refers to a dose having a maximum therapeutic effect in the range that can be safely used free from serious side effects, for example, determined by clinical trials, and specific example includes doses that are approved, recommended and advised by public institutions and associations such as PMDA; Pharmaceuticals and Medical Devices Agency, FDA; Food and Drug Administration), and EMA; European Medicines Agency, and described in the attached document, interview form and treatment guidelines, and the dose approved by any of public institutions of PMDA, FDA or EMA is preferable.

The administration schedule of the antitumor agent of the present invention can be properly selected depending on, for example, carcinoma and stage.

In the case of the FTD/TPI combination drug, an administration schedule of 5-day daily administration and 2-day rest are repeated twice, followed by rest for 2 weeks, or an administration schedule of 5-day daily administration and 9-day rest are repeated twice is preferable.

In the case of Compound 1 or a pharmaceutically acceptable salt thereof, the tegafur/gimeracil/oteracil potassium combination drug, and capecitabine, an administration schedule of 1- to 4-week administration and 1- to 2-week rest are repeated is preferable, an administration schedule of 2- to 3-week administration and 1-week rest are repeated is more preferable, and an administration schedule of 2-week administration and 1-week rest are repeated is particularly preferable.

In the case of nivolumab or atezolizumab, an administration schedule that administers at 3-week intervals is preferable.

The number of administrations of the antitumor agent of the present invention per day can be properly selected depending on, for example, carcinoma and stage.

The number of administrations is preferably twice a day in the case of FTD/TPI combination drug, twice a day in the case of Compound 1 or a pharmaceutically acceptable salt thereof, tegafur/gimeracil/oteracil potassium combination drug and capecitabine, and once a day in the case of nivolumab or atezolizumab.

The order of administration of the DNA function inhibitor and the immunomodulator of the present invention can be properly selected depending on, for example, carcinoma and stage, and either one may be administered first, and both may be administered simultaneously.

Specific examples of the cancer to be targeted by the antitumor agent of the present invention include head and neck cancer, gastrointestinal cancer (e.g., esophageal cancer, gastric cancer, duodenal cancer, liver cancer, biliary tract cancer (e.g., gallbladder/bile duct cancer), pancreatic cancer, small bowel cancer, and large bowel cancer (e.g., colorectal cancer, colon cancer, and rectal cancer)), lung cancer (e.g., non-small cell lung cancer, small cell lung cancer), breast cancer, ovarian cancer, uterine cancer (e.g., cervical cancer and endometrial cancer), renal cancer, bladder cancer, prostate cancer, and skin cancer. Here, the cancer includes not only a primary tumor but also a tumor derived from a solid cancer that has metastasized to other organs (such as liver). Among them, from the viewpoint of antitumor effects and side effects, the target of the antitumor agent of the present invention is preferably head and neck cancer, gastrointestinal cancer, lung cancer, breast cancer, renal cancer and skin cancer, more preferably gastrointestinal cancer, lung cancer, or breast cancer, more preferably large bowel cancer, gastric cancer, or lung cancer, and particularly preferably large bowel cancer. The antitumor agent of the present invention may be one used for postoperative adjuvant chemotherapy that is performed for preventing the recurrence after having extracted the tumor surgically, and also may be one used for preoperative adjuvant chemotherapy that is performed in advance for extracting the tumor surgically.

Since the administration method and the administration schedule are different in each active ingredient, and when all active ingredients of the DNA function inhibitor and the immunomodulator cannot be formulated into one dosage form, it is preferred that the antitumor agent of the present invention is separately formulated into a plurality of dosage forms for each active ingredient. Specifically, it is preferred that the FTD/TPI combination drug and the tegafur/gimeracil/oteracil potassium combination drug be formulated as combination drugs, and Compound 1 or a pharmaceutically acceptable salt thereof, capecitabine, the anti-PD-1 antibody, the anti-PD-L1 antibody or the anti-CTLA-4 antibody be formulated as a single agent.

In addition, as long as each active ingredient is administered according to the dose of the present invention, each preparation may be manufactured and sold together in a single package suitable for administration in combination, or each preparation may be manufactured and sold after being divided into separate package.

There is no particular limitation to the dosage form of the antitumor agent of the present invention, and it can be appropriately selected depending on the therapeutic purposes and include specifically, for example, oral preparations (e.g., tablets, coated tablets, powders, granules, capsules, and solutions), injections, suppositories, patches, and ointments. An oral preparation is preferable in the case of the FTD/TPI combination drug, Compound 1 or a pharmaceutically acceptable salt thereof, tegafur/gimeracil/oteracil potassium combination drug, and capecitabine. In the case of the anti-PD-1 antibody, anti-PD-L1 antibody, or the anti-CTLA-4 antibody, examples include the above dosage form, and an injection is preferable.

Depending on the dosage form, the antitumor agent of the present invention can be usually prepared by the known method using a pharmaceutically acceptable carrier, also for the DNA function inhibitor and the immunomodulator. Such a carrier includes various ones which are commonly used in conventional drugs, such as excipients, binders, disintegrators, lubricants, diluents, solubilizers, suspending agents, isotonic agents, pH adjusting agents, buffering agents, stabilizers, coloring agents, flavoring agents, and odor improving agents.

The present invention also relates to an antitumor effect potentiator containing a DNA function inhibitor for potentiating an antitumor effect of an immunomodulator on a cancer patient. The antitumor effect potentiator has a preparation form of the above antitumor agent.

The present invention also relates to an antitumor effect potentiator containing an immunomodulator for potentiating an antitumor effect of a DNA function inhibitor on a cancer patient. The antitumor effect potentiator has a preparation form of the above antitumor agent.

The present invention also relates to an antitumor agent containing a DNA function inhibitor for treating a cancer patient administered with an immunomodulator. The antitumor agent has the above preparation form.

The present invention also relates to an antitumor agent containing an immunomodulator for treating a cancer patient administered with a DNA function inhibitor. The antitumor agent has the above preparation form.

The "treatment" includes postoperative adjuvant chemotherapy that is performed for preventing the recurrence after having extracted the tumor surgically and preoperative adjuvant chemotherapy that is performed in advance for extracting the tumor surgically.

The present invention also relates to an antitumor agent containing a DNA function inhibitor, which is used in combination with an immunomodulator on a cancer patient. The antitumor agent has the above preparation form.

The present invention also relates to an antitumor agent containing an immunomodulator, which is used in combination with a DNA function inhibitor on a cancer patient. The antitumor agent has the above preparation form.

The present invention also relates to a kit preparation containing an antitumor agent containing a DNA function inhibitor, and an instruction for use describing that the DNA function inhibitor and an immunomodulator are to be administered to a cancer patient in combination. The term "instruction for use" may be any one as long as it describes the above dose; however, an instruction for use, in which the above dose is recommended though legal binding force does not matter, is preferable. The instruction for use includes specifically, for example, a package insert, and a pamphlet. Also, a kit preparation containing an instruction for use may be one in which an instruction for use is printed on or attached to the package of the kit preparation, or may be one in which an instruction for use is enclosed in a package of the kit preparation together with an antitumor agent.

EXAMPLES

Hereinafter, the present invention will be explained in further detail by way of examples and reference examples. However, this invention should not be limited to these examples in any manner, and many variations can be employed by a person with ordinary skill in the art within the technical concept of the present invention.

Reference Example 1

Cultured cells ($1 \times 10^7$ cells/mouse) derived from human large bowel cancer cell line (KM20C) were intraperitoneally transplanted into 5 to 6 week old BALB/cA Jcl-nu mice. The mice were divided into groups so that the mean body weight of each group might be equal, and the date of grouping (n=10) was designated as Day 0.

FTD/TPI combination drug (a mixture of FTD and TPI in a molar ratio of 1:0.5, hereinafter the same) was prepared for administration in an amount of 75, 100, 150, 300, and 450 mg/kg/day as FTD. The drug administration started on Day 3, and a 5-day daily oral administration of the FTD/TPI combination drug with 2-day rest was performed for 6 weeks.

As an index of the antitumor effect, the number of mice surviving in each groups and the survival time and increased life span of each group were compared. The increased life span (ILS) was calculated as follows.

ILS (%) [{(mean life span of the administration group)/(mean life span of the untreated group)}−1]×100

The results are shown in Table 1.

TABLE 1

| Group | Dose (in terms of FTD, mg/kg/day) | Mean life span (day) Mean ± SD | ILS (%) |
|---|---|---|---|
| Untreated | — | 40.0 ± 4.3 | — |
| FTD/TPI Combination drug | 75 | 50.0 ± 9.1 | 25.0 |
| FTD/TPI Combination drug | 100 | 75.8 ± 42.6 | 89.5 |
| FTD/TPI Combination drug | 150 | 125.7 ± 64.8 | 214.3 |
| FTD/TPI Combination drug | 300 | 75.6 ± 17.5 | 89.0 |
| FTD/TPI Combination drug | 450 | 54.1 ± 18.3 | 35.3 |

As described in Table 1, for the FTD/TPI combination drug, an effect of extending life span in all groups of 75 to 450 mg/kg/day as the FTD amount is observed, and among them, life span is longest in the group of 150 mg/kg/day, thus the recommended dose (RD) of the FTD/TPI combination drug in mice is 150 mg/kg/day as FTD. Thus, it was shown that the FTD/TPI combination drug exhibits an extending effect of life span at least in a dose of 50 to 300% of RD.

While, it is known that RD when the FTD/TPI combination drug is administered alone in human is 70 mg/m$^2$/day as FTD. Thus, the dose of the FTD/TPI combination drug as FTD corresponds to 150 mg/kg/day in mice and 70 mg/m$^2$/day in humans.

Reference Example 2

Mouse large bowel cancer cell line (CMT-93) was transplanted into the right side of the chest of 5 to 6 weeks old C57BL/6 mice after birth. After tumor transplantation, the major axis (mm) and minor axis (mm) of tumor were measured, and the tumor volume (TV) was calculated. Then, the mice were divided into groups so that the mean TV of each group might be equal and the day when the grouping (n=6) was performed was designated as Day 0.

An anti-mouse PD-1 antibody (clone RMP1-14, manufactured by BioXCell, hereinafter the same) was prepared for administration in an amount of 0.1 mg/body/day, that is a dose in which the antitumor effect is reported in mouse (Clin Cancer Res. 2013 Oct. 15; 19(20): 5626-35.). The anti-mouse PD-1 antibody was intraperitoneally administered on Day 1, Day 5, and Day 9.

As an index of the antitumor effect, TV on Day 0, 4, 8, 11, 15, 18, 22, 25 and 28 in each group was calculated, and the relative tumor volume (RTV) on Day 0 was determined by the following formula and compared to the RTV of the untreated (control) group.

TV (mm$^2$)=(major axis×minor axis$^2$)/2

RTV=(TV on Day 28)/(TV on Day 0)

The RTV is plotted for each measurement date, and the result of comparing the time (day)-course change of RTV of the untreated group and the anti-mouse PD-1 antibody single administration group is shown in FIG. 1.

Tumor growth inhibition (TGI) rate based on the RTV value on Day 28 was calculated according to the following formula.

TGI (%)=[1−(mean RTV of the treated group)/(mean RTV of the untreated group)]×100

For evaluating the effect with a single agent, it was determined that there was an enhancing effect when the mean RTV value of the single administration group was statistically significantly (Closed testing procedure; Intersection-Union Test p<0.01) smaller than the mean RTV value of the untreated (control) group.

The results were shown in Table 2.

TABLE 2

| Drug | Dose | Treatment | TV[a] (mm$^3$, mean ± SD) | RTV[b] (mean ± SD) | TGI[c] (%) |
|---|---|---|---|---|---|
| Control | — | Day 1~14, p.o. | 574.76 ± 102.51 | 7.85 ± 1.68 | — |
| Anti-mousePD-1 antibody | 0.1 mg/body/day | Day 1, 5, 9, i.p. | 78.16 ± 12.55 | 1.07 ± 0.21 ** | 86.4 |

** p < 0.01 with Aspin-Welch's t-test as compared with the control group.

[a] Tumor volume (TV) on Day 28 was calculated according to the following formula: TV = (length) × (width) × (width)/2

[b] Relative tumor volume (RTV) on Day 28 was calculated as the ratio of TV on Day 28 to that on Day 0 according to the following formula: RTV = (TV on Day 28)/(TV on Day 0)

[c] Tumor growth inhibition rate (TGI) on Day 28 on the basis of RTV was calculated according to the following formula: TGI (%) = [(mean RTV of the control group) − (mean RTV of the treated group)]/(mean RTV of the control group) × 100

SD: standard deviation

Control group was given the vehicle for FTD · TPI

While, as an index indicating systematic toxicity due to drug administration, the body weight change (BWC) was used. BWC was calculated according to the following formula, and the mean BWC values were shown in FIG. 2 and Table 3.

BWC (%)=[(Body weight of mouse on Day 28)−(Body weight of mouse on Day 0)]/(Body weight of mouse on Day 0)×100

TABLE 3

| Drug | Dose | Treatment | No. of Animals | No. of Death | BWC[a] (%, mean ± SD) |
|---|---|---|---|---|---|
| Control | — | Day 1~14, p.o. | 6 | 0 | 16.87 ± 3.73 |
| Anti-mousePD-1 antibody | 0.1 mg/body/day | Day 1, 5, 9, i.p. | 6 | 0 | 11.88 ± 2.07 |

** $p < 0.01$ with Aspin-Welch's t-test as compared with the control group.
[a] Body weight change (BWC, %; mean ± SD) on Day 28 were calculated according to the following formula: BWC (%) = [(BW on Day 28) − (BW on Day 0)]/(BW on Day 0) × 100
SD: standard deviation
Control group was given the vehicle for FTD · TPI As shown in FIG. 1, FIG. 2, Table 2 and Table 3, when the anti-mouse PD-1 antibody was 0.1 mg/body/day, a statistically significant antitumor effect was shown. In the anti-mouse PD-1 antibody single administration group, serious weight reduction exceeding −20% was not observed, and the side effects were acceptable degree.

Example 1

Combinatorial Use of FTD/TPI Combination Drug and Anti-Mouse PD-1 Antibody

Mouse large bowel cancer cell line (CMT-93) was transplanted into the right side of the chest of 5 to 6 weeks old C57BL/6 mice after birth. After the tumor transplantation, the major axis (mm) and minor axis (mm) of tumor were measured, and the tumor volume (TV) was calculated. Then, the mice were divided into groups so that the mean TV of each group might be equal and the day of grouping (n=6) was designated as Day 0.

An FTD/TPI combination drug was prepared for administration in an amount of 150 mg/kg/day as the dose of FTD. An anti-mouse PD-1 antibody was prepared for administration in an amount of 0.1 mg/body/day. The FTD/TPI combination drug was orally administered daily on Day 1 to 14, and the anti-mouse PD-1 antibody was intraperitoneally administered on Day 1, Day 5, and Day 9.

As an index of the antitumor effect, TV on Day 0, 4, 7, 11, 15, 18, 22, 26 and 28 in each group was calculated, and the relative tumor volume (RTV) on Day 0 was determined by the above formula and compared to the RTV of the untreated (control) group.

The above RTV was plotted for each measurement date. The result of comparing the time (day)-course change of RTV between the untreated group, the FTD/TPI combination drug administration group, the anti-mouse PD-1 antibody single administration group, and the co-administration group of the FTD/TPI combination drug and the anti-mouse PD-1 antibody is shown in FIG. 3.

Tumor growth inhibition (TGI) rate based on the RTV value on Day 28 was calculated.

It was determined that there is an enhancing effect when the mean RTV value of the co-administration group is statistically significantly (Closed testing procedure; Intersection-Union Test $p<0.01$) smaller than the mean RTV value of the individual single administration group.

The results were shown in Table 4.

TABLE 4

| Drug | Dose | Treatment | No. of Animals | No. of Death | TV[a] (mm³, mean ± SD) | RTV[b] (mean ± SD) | TGI[c] (%) |
|---|---|---|---|---|---|---|---|
| Control | — | Day 1~14, p.o. | 6 | 0 | 598.94 ± 84.67 | 5.05 ± 0.49 | — |
| Anti-mouse PD-1 antibody | 0.1 mg/body/day | Day 1, 5, 9, i.p. | 6 | 0 | 77.85 ± 12.73 | 0.68 ± 0.11** | 86.5 |
| FTD · TPI | 150 mg/kg/day | Day 1~14, p.o. | 6 | 0 | 283.48 ± 72.79 | 2.45 ± 0.60** | 51.5 |
| Anti-mouse PD-1 antibody + FTD · TPI | 0.1 mg/body/day + 150 mg/kg/day | Day 1, 5, 9, i.p. + Day 1~14, p.o. | 6 | 0 | 9.87 ± 2.98 | 0.09 ± 0.03**##$$ | 98.2 |

**$p < 0.01$ with Aspin-Welch's t-test as compared with the control group.
$p < 0.01$ with Aspin-Welch's t-test as compared with the Anti-mouse PD-1 group.
$$$p < 0.01$ with Aspin-Welch's t-test as compared with the FTD · TPI group.
[a] Tumor volume (TV) on Day 28 was calculated according to the following formula: TV = (length) × (width) × (width)/2
[b] Relative tumor volume (RTV) on Day 28 was calculated as the ratio of TV on Day 28 to that on Day 0 according to the following formula: RTV = (TV on Day 28)/(TV on Day 0)
[c] Tumor growth inhibition rate (TGI) on Day 28 on the basis of RTV was calculated according to the following formula: TGI (%) = [(mean RTV of the control group) − (mean RTV of the treated group)]/(mean RTV of the control group) × 100
SD: standard deviation
Control group was given the vehicle for FTD · TPI As an index of systemic toxicity due to drug administration, the body weight change (BWC) was calculated, and the mean BWC value and the daily variation thereof were shown in Table 5 and FIG. 4, respectively.

TABLE 5

| Drug | Dose | Treatment | No. of Animals | No. of Death | BWC[a] (%, mean ± SD) |
|---|---|---|---|---|---|
| Control | — | Day 1~14, p.o. | 6 | 0 | 10.79 ± 2.73 |
| Anti-mouse PD-1 antibody | 0.1 mg/body/day | Day 1, 5, 9, i.p. | 6 | 0 | 11.46 ± 3.12 |
| FTD · TPI | 150 mg/kg/day | Day 1~14, p.o. | 6 | 0 | 12.70 ± 4.84 |

TABLE 5-continued

| Drug | Dose | Treatment | No. of Animals | No. of Death | BWC[a] (%, mean ± SD) |
|---|---|---|---|---|---|
| Anti-mouse PD-1 antibody + FTD · TPI | 0.1 mg/body/day + 150 mg/kg/day | Day 1, 5, 9, i.p. + Day 1~14, p.o | 6 | 0 | 10.48 ± 4.64 |

** p < 0.01 with Aspin-Welch's t-test as compared with the control group.
[a]Body weight change (BWC, %; mean ± SD) on Day 28 were calculated according to the following formula: BWC (%) = [(BW on Day 28) − (BW on Day 0)]/(BW on Day 0) × 100
SD: standard deviation
Control group was given the vehicle for FTD · TPI As shown in FIG. 3, FIG. 4, Table 4 and Table 5, by the combinatorial use of the FTD/TPI combination drug and the anti-mouse PD-1 antibody, a statistically significantly remarkably potentiated antitumor effect was confirmed.

It was confirmed that, while the TGI in the combinatorial use expected when assuming that the effect of combinatorial use of both drugs was additive was 93.4%, actually, a more excellent antitumor effect like 98.2% was confirmed. Thus, the effect of combinatorial use the FTD/TPI combination drug and the anti-mouse PD-1 antibody was shown to be synergistic effect.

In the co-administration group of the FTD/TPI combination drug and the anti-mouse PD-1 antibody, serious weight reduction exceeding −20% was not observed, and the side effects were acceptable degree.

Example 2

Combinatorial Use of FTD/TPI Combination Drug and Anti-Mouse PD-1 Antibody 75, 100, 150 mg/kg/day (as FTD) of the FTD/TPI combination drug and 0.1 mg/body/day of the anti-mouse PD-1 antibody were administered to mice into which mouse large bowel cancer cell line (CMT-93) was transplanted in accordance with Example 1, and antitumor effects and weight reductions were measured. The results are shown in FIGS. 5 to 13, Table 6 and Table 7.

TABLE 6

| Drug | Dose | Treatment | No. of Animals | No. of Death | TV[a] (mm³, mean ± SD) | RTV[b] (mean ± SD) | TGI[c] (%) |
|---|---|---|---|---|---|---|---|
| Control | — | Day 1~14, p.o. | 5 | 0 | 705.23 ± 63.01 | 6.35 ± 0.61 | — |
| Anti-mouse PD-1 antibody | 0.1 mg/body/day | Day 1, 5, 9, i.p. | 5 | 0 | 129.19 ± 51.89 | 1.16 ± 0.38** | 81.7 |
| FTD · TPI | 75 mg/kg/day | Day 1~14, p.o. | 5 | 0 | 469.25 ± 92.63 | 4.23 ± 0.61** | 33.4 |
| FTD · TPI | 100 mg/kg/day | Day 1~14, p.o. | 5 | 0 | 374.77 ± 43.77 | 3.42 ± 0.24** | 46.1 |
| FTD · TPI | 150 mg/kg/day | Day 1~14, p.o. | 5 | 0 | 282.79 ± 53.79 | 2.57 ± 0.35** | 59.5 |
| Anti-mouse PD-1 antibody + FTD · TPI | 0.1 mg/body/day + 75 mg/kg/day | Day 1, 5, 9, i.p. + Day 1~14, p.o. | 5 | 0 | 56.04 ± 12.67 | 0.52 ± 0.14**##$ | 91.8 |
| Anti-mouse PD-1 antibody + FTD · TPI | 0.1 mg/body/day + 100 mg/kg/day | Day 1, 5, 9, i.p. + Day 1~14, p.o. | 5 | 0 | 29.18 ± 10.77 | 0.27 ± 0.09**##$$ | 95.7 |
| Anti-mouse PD-1 antibody + FTD · TPI | 0.1 mg/body/day + 150 mg/kg/day | Day 1, 5, 9, i.p. + Day 1~14, p.o. | 5 | 0 | 11.08 ± 2.39 | 0.10 ± 0.02**##$$ | 98.4 |

**p < 0.01 with Aspin-Welch's t-test as compared with the Control group.
p < 0.01 with Aspin-Welch's t-test as compared with the Anti-mouse PD-1 mAb group.
$, $$p < 0.05, p < 0.01 with Aspin-Welch's t-test as compared with the FTD · TPI group.
[a]Tumor volume (TV) on Day 28 was calculated according to the following formula: TV = (length) × (width) × (width)/2
[b]Relative tumor volume (RTV) on Day 28 was calculated as the ratio of TV on Day 28 to that on Day 0 according to the following formula: RTV = (TV on Day 28)/(TV on Day 0)
[c]Tumor growth inhibition rate (TGI) on Day 28 on the basis of RTV was calculated according to the following formula: TGI (%) = [(mean RTV of the control group) − (mean RTV of the treated group)]/(mean RTV of the control group) × 100
SD: standard deviation
Control group was given the vehicle for FTD · TPI

TABLE 7

| Drug | Dose | Treatment | No. of Animals | No. of Death | BWC[a] (%, mean ± SD) |
|---|---|---|---|---|---|
| Control | — | Day 1~14, p.o. | 5 | 0 | 13.89 ± 2.25 |
| Anti-mouse PD-1 antibody | 0.1 mg/body/day | Day 1, 5, 9, i.p. | 5 | 0 | 15.23 ± 3.16 |
| FTD · TPI | 75 mg/kg/day | Day 1~14, p.o. | 5 | 0 | 13.51 ± 2.52 |
| FTD · TPI | 100 mg/kg/day | Day 1~14, p.o. | 5 | 0 | 13.40 ± 1.94 |
| FTD · TPI | 150 mg/kg/day | Day 1~14, p.o. | 5 | 0 | 11.51 ± 1.55 |
| Anti-mouse PD-1 antibody + FTD · TP1 | 0.1 mg/body/day + 75 mg/kg/day | Day 1, 5, 9, i.p. + Day 1-14, p.o. | 5 | 0 | 12.00 ± 1.83 |
| Anti-mouse PD-1 antibody + FTD · TPI | 0.1 mg/body/day + 100 mg/kg/day | Day 1, 5, 9, i.p. + Day 1~14, p.o. | 5 | 0 | 10.71 ± 1.73 |
| Anti-mouse PD-1 antibody + FTD · TPI | 0.1 mg/body/day + 150 mg/kg/day | Day 1, 5, 9, i.p. + Day 1~14, p.o. | 5 | 0 | 10.40 ± 2.34 |

** p < 0.01 with Aspin-Welch's t-test as compared with the Control group.
[a]Body weight change (BWC, %; mean ± SD) on Day 28 were calculated according to the following formula: BWC (%) = [(BW on Day 28) − (BW on Day 0)]/(BW on Day 0) × 100
SD: standard deviation
Control group was given the vehicle for FTD · TPI As shown in FIGS. 5 to 13, Table 6 and Table 7, statistically significantly remarkably potentiated antitumor effects were confirmed in all combinatorial use groups of the FTD/TPI combination drug and the anti-mouse PD-1 antibody.

It was confirmed that, while the TGI in the combinatorial use expected when assuming that the effect of combinatorial use of both drugs was additive was 87.8%, 90.1%, and 92.6% respectively in the groups of 75, 100, 150 mg/kg/day as FTD, actually, more excellent antitumor effects like 91.8%, 95.7%, and 98.4% were confirmed. Thus, the effect of combinatorial use of the FTD/TPI combination drug and the anti-mouse PD-1 antibody was shown to be synergistic effect.

In all co-administration groups, serious weight reduction exceeding −20% was not observed, and the side effects were acceptable degree.

Further, the significant potentiation in the antitumor effect by the PD-1 antibody, even with a halved FTD amount, was a unexpected result.

Furthermore, in the combinatorial use group with 150 mg/kg/day of FTD, disappearance of tumors was confirmed in 4 mice out of 5 mice. This verifies that the antitumor effect is extremely high at the time of combinatorial use.

Example 3

Combinatorial Use of FTD/TPI Combination Drug and Anti-Mouse PD-L1 Antibody 150 mg/kg/day (as FTD) of the FTD/TPI combination drug and 0.1 and 0.2 mg/body/day of the anti-mouse PD-L1 antibody (clone 10F.9G2, manufactured by BioXCell, hereinafter the same) were administered to mice into which mouse large bowel cancer line (CMT-93) was transplanted in accordance with Example 1, and antitumor effects and weight reductions were measured. The results are shown in FIGS. 14 and 15, Table 8 and Table 9.

TABLE 8

| Drug | Dose | Treatment | No. of Animals | No. of Death | TV[a] (mm³, mean ± SD) | RTV[b] (mean ± SD) | TGI[c] (%) |
|---|---|---|---|---|---|---|---|
| Control | — | Day 1~14, p.o. | 6 | 0 | 759.19 ± 134.59 | 7.58 ± 1.51 | — |
| Anti-mouse PD-L1 antibody 0.1 mg/body/day | 0.1 mg/body/day | Day 1, 5, 9, i.p. | 6 | 0 | 409.24 ± 113.84 | 4.05 ± 0.95** | 46.6 |
| Anti-mouse PD-L1 antibody 0.2 mg/body/day | 0.2 mg/body/day | Day 1, 5, 9, i.p. | 6 | 0 | 322.73 ± 83.63 | 3.24 ± 0.98** | 57.3 |
| FTD · TPI 150 mg/kg/day | 150 mg/kg/day | Day 1~14, p.o. | 6 | 0 | 357.40 ± 66.72 | 3.59 ± 0.84** | 52.6 |
| Anti-mouse PD-L1 antibody + FTD · TPI | 0.1 mg/body/day + 150 mg/body/day | Day 1, 5, 9, i.p. + Day 1~14, p.o. | 6 | 0 | 54.37 ± 36.25 | 0.53 ± 0.32**##$$ | 93.0 |
| Anti-mouse PD-L1 antibody + FTD · TPI | 0.2 mg/body/day + 150 mg/body/day | Day 1, 5, 9, i.p. + Day 1~14, p.o. | 6 | 0 | 51.90 ± 49.81 | 0.49 ± 0.46**##$$ | 93.5 |

**p < 0.01 with Aspin-Welch's t-test as compared with the Control group.

p < 0.01 with Aspin-Welch's t-test as compared with the Anti-mouse PD-1 mAb group.

$$p < 0.01 with Aspin-Welch's t-test as compared with the FTD · TPI group.

[a]Tumor volume (TV) on Day 28 was calculated according to the following formula: TV = (length) × (width) × (width)/2

[b]Relative tumor volume (RTV) on Day 28 was calculated as the ratio of TV on Day 28 to that on Day 0 according to the following formula: RTV = (TV on Day 28)/(TV on Day 0)

[c]Tumor growth inhibition rate (TGI) on Day 28 on the basis of RTV was calculated according to the following formula: TGI (%) = [(mean RTV of the control group) − (mean RTV of the treated group)]/(mean RTV of the control group) × 100

SD: standard deviation

Control group was given the vehicle for FTD · TPI

TABLE 9

| Drug | Dose | Treatment | No. of Animals | No. of Death | BWC[a] (%, mean ± SD) |
|---|---|---|---|---|---|
| Control | — | Day 1~14, p.o. | 6 | 0 | 15.85 ± 5.72 |
| Anti-mousePD-L1 antibody 0.1 mg/body/day | 0.1 mg/body/day | Day 1, 5, 9, i.p. | 6 | 0 | 16.31 ± 2.47 |
| Anti-mousePD-L1 antibody 0.2 mg/body/day | 0.2 mg/body/day | Day 1, 5, 9, i.p. | 6 | 0 | 12.16 ± 3.94 |
| FTD · TPI 150 mg/kg/day | 150 mg/kg/day | Day 1~14, p.o. | 6 | 0 | 8.56 ± 1.88 |
| Anti-mousePD-L1 antibody + FTD · TPI | 0.1 mg/body/day + 150 mg/body/day | Day 1, 5, 9, i.p. + Day 1~14, p.o. | 6 | 0 | 5.52 ± 6.42 |
| Anti-mousePD-L1 antibody + FTD · TPI | 0.2 mg/body/day + 150 mg/body/day | Day 1, 5, 9, i.p. + Day 1~14, p.o. | 6 | 0 | 7.82 ± 1.55 |

** p < 0.01 with Aspin-Welch's t-test as compared with the Control group.

[a]Body weight change (BWC, %; mean ± SD) on Day 28 were calculated according to the following formula: BWC (%) = [(BW on Day 28) − (BW on Day 0)]/(BW on Day 0) × 100

SD: standard deviation

Control group was given the vehicle for FTD · TPI

As shown in FIGS. 14 and 15, Table 8 and Table 9, statistically significantly remarkably potentiated antitumor effects were confirmed in all combinatorial use groups of the FTD/TPI combination drug and the anti-mouse PD-L1 antibody.

Additionally, it was confirmed that, while the TGI in the combinatorial use expected when assuming that the effect of combinatorial use of both drugs was additive was 74.7% and 79.8% respectively in the groups of 0.1 and 0.2 mg/body/day of the anti-mouse PD-L1 antibody, actually, more excellent antitumor effects like 93.0% and 93.5% were confirmed. Thus, the effect of combinatorial use of the FTD/TPI combination drug and the anti-mouse PD-L1 antibody was shown to be synergistic effect.

In all co-administration groups, serious weight reduction exceeding −20% was not observed, and the side effects were acceptable degree.

Example 4

Combinatorial Use of S-1+Compound 1 and Anti-Mouse PD-1 Antibody

Mouse large bowel cancer cell line (CMT-93) was transplanted into the right side of the chest of 5 to 6 weeks old C57BL/6NJcl mice after birth. After the tumor transplantation, the major axis (mm) and minor axis (mm) of tumor were measured, and the tumor volume (TV) was calculated. Then, the mice were divided into groups so that the mean TV of each group might be equal and the day of grouping (n=8) was designated as Day 0.

The tegafur/gimeracil/oteracil potassium combination drug ("S-1", tegafur gimeracil: oteracil=1:0.4:1 (molar ratio), hereinafter the same) and Compound 1 ((R)-N-(1-(3-(cyclopentyloxy)phenyl)ethyl)-3-((2,4-dioxo-3,4-dihydropyrimidin-1(2H)-yl)methoxy)propane-1-sulfonamide) were suspended in an aqueous solution of 0.5% hydroxypropylmethyl cellulose. S-1 dose was set to be 6.9 mg/kg/day (tegafur amount) (Anticancer Res. 32:2807-2812 (2012)), and Compound 1 was set to be 2,400 mg/kg/day, which is presumed to be the maximum dose administerable to a mouse. The anti-mouse PD-1 antibody was prepared to be 0.1 mg/body/day.

S-1 and a mixed administration solution of S-1 and Compound 1 were orally administered daily once a day for 28 days starting from the following day of grouping, and the anti-mouse PD-1 antibody was intraperitoneally administered on Day 1, 8, 15, and 22. The control group was orally administered with the aqueous solution of 0.5% hydroxypropylmethyl cellulose daily once a day for 28 days.

As an index of the antitumor effect, TV was calculated in each group to determine the relative tumor volume (RTV) to Day 0, and Treated/control (T/C, %) was calculated by the following formula using mean values of the RTV of the drug administration groups and the untreated (control) group to evaluate antitumor effects.

TV (mm$^3$)=(major axis x minor axis$^2$)/2

RTV=(TV on Day 29)/(TV on Day 0)

T/C (%)=(mean RTV on Day 29 of drug administration groups)/(mean RTV on Day 29 of untreated group)×100

The above RTV was plotted on each measurement date. The result of comparing the time (day)-course change of RTV between each administration group is shown in FIG. 16 and Table 10.

TABLE 10

| Drug | Dose (mg/kg/day) | Treatment | TV[a] (mm$^3$, mean ± SD) | RTV[b] (mean ± SD) | T/C[c] (%) |
|---|---|---|---|---|---|
| Control(0.5 w/v % HPMC) | — | Day 1-28, p.o., q.d. | 396.60 ± 49.08 | 3.51 ± 0.54 | 100.0 |
| S-1 | 6.9 m/kg/day | Day 1-28, p.o., q.d. | 181.26 ± 63.27 | 1.60 ± 0.56 *** | 45.6 |
| anti-mouse PD-1 antibody | 0.1 mg/body/day | Day 1, 8, 15, 22, i.p. | 106.03 ± 61.93 | 0.93 ± 0.54 *** | 26.5 |
| S-1/compound 1 | 6.9 mg/kg/day/ 2400 mg/kg/day | Day 1-28, p.o., q.d./ Day 1-28, p.o., q.d. | 171.99 ± 102.15 | 1.50 ± 0.86 *** | 42.7 |
| S-1/anti-mouse PD-1 antibody | 6.9 mg/kg/day/ 0.1 mg/body/day | Day 1-28, p.o., q.d./ Day 1, 8, 15, 22, i.p. | 107.95 ± 94.43 | 0.93 ± 0.78 *** | 26.5 |
| S-1/compound 1/ anti-mouse PD-1 antibody | 6.9 mg/kg/day/ 2400 mg/kg/day/ 0.1 mg/body/day | Day 1-28, p.o., q.d./ Day 1-28, p.o., q.d./ Day 1, 8, 15, 22, i.p. | 38.53 ± 30.71 | 0.34 ± 0.27 ***#$$ | 9.7 |

*** $p < 0.001$ with Aspin-Welch's t-test as compared with the control group
$p < 0.05$ with Aspin-Welch's t-test as compared with the anti-mouse PD-1 antibody group
$$$p < 0.01$ with Aspin-Welch's t-test as compared with the S-1/compound 1 group
[a] Tumor volume (TV) on Day 29 was calculated according to the following formula: TV = (length) × (width) × (width)/2
[b] Relative tumor volume (RTV) on Day 29 was calculated as the ratio of TV on Day 29 to that on Day 0 according to the following formula: RTV = (TV on Day 29)/(TV on Day 0)
[c] Treated/Control (T/C) on Day 29 on the basis of RTV was calculated according to the following formula: T/C (%) = (mean RTV in administration group)/(mean RTV in control group) × 100
SD: standard deviation As an index indicating systematic toxicity due to drug administration, the body weight change (BWC) was used. BWC was calculated according to the following formula, and the mean BWC values were shown in FIG. 17 and Table 11.

BWC (%)=([(mouse body weight on Day 29)−(mouse body weight on Day 0)]/(mouse body weight on Day 0))×100

TABLE 11

| Drug | Dose (mg/kg/day) | Treatment | No. of Animals | No. of Death | BWC [a] (%, Mean ± SD) |
|---|---|---|---|---|---|
| Control(0.5 w/v % HPMC) | — | Day 1-28, p.o., q.d. | 8 | 0 | 8.74 ± 12.45 |
| S-1 | 6.9 mg/kg/day | Day 1-28, p.o., q.d. | 8 | 0 | 8.43 ± 3.71 |
| anti-mouse PD-1 antibody | 0.1 mg/body/day | Day 1, 8, 15, 22, i.p. | 8 | 0 | 16.34 ± 3.37 |
| S-1/compound 1 | 6.9 mg/kg/day/ 2400 mg/kg/day | Day 1-28, p.o., q.d./ Day 1-28, p.o., q.d. | 8 | 0 | 10.28 ± 4.99 |
| S-1/anti-mouse PD-1 antibody | 6.9 mg/kg/day/ 0.1 mg/body/day | Day 1-28, p.o., q.d./ Day 1, 8, 15, 22, i.p. | 8 | 0 | 11.26 ± 1.77 |
| S-1/compound 1/ anti-mouse PD-1 antibody | 6.9 mg/kg/day/ 2400 mg/kg/day/ 0.1 mg/body/day | Day 1-28, p.o., q.d./ Day 1-28, p.o., q.d./ Day 1, 8, 15, 22, i.p. | 8 | 0 | 9.07 ± 4.27 |

[a] Body weight change (BWC) (%; mean ± SD) on each Day was calculated according to the following formula: BWC(%) = [(BW on Day 29) − (BW on Day 0)]/(BW on Day 0) × 100
SD: standard deviation As shown in FIG. 17 and Table 11, statistically significant antitumor effects were observed in all drug administration groups when compared with the control group, and serious weight reduction exceeding −20% was not observed, and the side effects were acceptable degree.

The S-1+anti-mouse PD-1 antibody administration group and the anti-mouse PD-1 antibody administration group had the same T/C (%), thus failing to confirm an apparent potentiating effect.

While, in the comparison with the S-1+Compound 1+anti-mouse PD-1 antibody administration group, the S-1+ Compound 1 administration group, and the anti-mouse PD-1 antibody administration group, the 3-drug co-administration group was found to have a statistically significant effect of combinatorial use to any groups.

Given the above results, it is revealed that S-1 which is a fluorinated pyrimidine antimetabolite does not notably potentiate the antitumor effect of the anti-PD-1 antibody as a single agent but notably potentiates the antitumor effect of the anti-PD-1 antibody when used in combination with Compound 1 which is a dUTPase inhibitor. Thus, the results of the present tests indicate that the DNA function inhibitor can potentiate the antitumor effect of the anti-PD-1 antibody.

Here, the present invention is not limited to each of embodiments and examples described above, and various modifications can be employed within the scope shown in the claims. Embodiments obtained by appropriately combining technical means each disclosed in different embodiments are also within the technical scope of the present invention. All of the scientific literatures and reference literatures described herein are hereby incorporated by reference.

The invention claimed is:

1. A method for treating a tumor, comprising:
    administering effective doses of a DNA function inhibitor and an immunomodulator to a subject in need thereof,
    wherein the DNA function inhibitor is a combination drug comprising trifluridine and tipiracil hydrochloride in a molar ratio of 1:0.5, and
    the immunomodulator is a PD-1 pathway antagonist which is at least one selected from the group consisting of an anti-PD-1 antibody, and an anti-PD-L1 antibody.

2. The method according to claim 1,
    wherein the dose per day of the combination drug is from 50 to 115% of the recommended dose when administered alone.

3. The method according to claim 1,
    wherein the dose per day of the combination drug is from 35 to 80 mg/m$^2$ day as trifluridine.

4. The method according to claim 1, wherein the cancer to be targeted is gastrointestinal cancer, lung cancer, or breast cancer.

5. The method according to claim 1, wherein the cancer to be targeted is large bowel cancer.

6. The method according to claim 1, wherein anti-PD-1 antibody is nivolumab or pembrolizumab.

7. The method according to claim 1, wherein the anti-PD-L1 antibody is atezolizumab, durvalumab, or avelumab.

8. The method according to claim 1, wherein the cancer to be targeted is gastric cancer.

9. A method for potentiating an antitumor effect of an immunomodulator, comprising:
    administering an effective dose of a DNA function inhibitor to a subject in need thereof,
    wherein the DNA function inhibitor is a combination drug comprising trifluridine and tipiracil hydrochloride in a molar ratio of 1:0.5, and
    the immunomodulator is at least one selected from the group consisting of an anti-PD-1 antibody, and an anti-PD-L1 antibody.

10. The method according to claim 9,
    wherein the dose per day of the combination drug is from 35 to 115% of the recommended dose when administered alone.

11. The method according to claim 9,
    wherein the dose per day of the combination drug is from 35 to 80 mg/m$^2$/day as trifluridine.

12. The method according to claim 9, wherein the cancer to be targeted is gastrointestinal cancer, lung cancer, or breast cancer.

13. The method according, to claim 9, wherein the cancer to be targeted is large bowel cancer.

14. The method according to claim 9, wherein the cancer to be targeted is gastric cancer.

15. The method of claim 9, wherein the immunomodulator is at least one selected from the group consisting of nivolumab and pembrolizumab.

16. The method of claim 9, wherein the immunomodulator is at least one selected from the group consisting of nivolumab, pembrolizumab, atezolizumab, durvalumab, and avelumab.

17. A method for treating a cancer patient administered with an immunomodulator, comprising:
    administering an effective dose of a DNA function inhibitor to a subject in need thereof,
    wherein the DNA function inhibitor is a combination drug comprising trifluridine and tipiracil hydrochloride in a molar ratio of 1:0.5, and the immunomodulator is at least one selected from the group consisting of an anti-PD-1 antibody, an anti-PD-L1 antibody.

18. The method according to claim 17, wherein the dose per day of the combination drug is from 50 to 115% of the recommended dose when administered alone.

19. The method according to claim 17, wherein the dose per day of the combination drug is from 35 to 80 mg/m$^2$/day as trifluridine.

20. The method according to claim 17, wherein the cancer to be targeted is gastrointestinal cancer, lung cancer, or breast cancer.

21. The method according to claim 17, wherein the cancer to be targeted is large bowel cancer.

22. The method according to claim 17, wherein the cancer to be targeted is gastric cancer.

23. The method of claim 17, wherein the immunomodulator is at least one selected from the group consisting of nivolumab, pembrolizumab, atezolizumab, durvalumab, and avelumab.

24. The method of claim 17, wherein the immunomodulator is at least one selected from the group consisting of nivolumab and pembrolizumab.

25. A method for treating a tumor in combination with using an immunomodulator, comprising:
administering an effective dose of a DNA function inhibitor to a subject in need thereof,
wherein the DNA function inhibitor is a combination drug comprising trifluridine and tipiracil hydrochloride in a molar ratio of 1:0.5, and
the immunomodulator is at least one selected from the group consisting of an anti-PD-1 antibody, an anti-PD-L1 antibody.

26. The method of claim 25, wherein the immunomodulator is at least one selected from the group consisting of nivolumab, pembrolizumab, atezolizumab, durvalumab, and avelumab.

27. The method according to claim 25, wherein the dose per day of the combination drug is from 50 to 115% of the recommended dose when administered alone.

28. The method according to claim 25, wherein the dose per day of the combination drug is from 35 to 80 mg/m$^2$/day as trifluridine.

29. The method according to claim 25, wherein the cancer to be targeted is gastrointestinal cancer, lung cancer, or breast cancer.

30. The method according to claim 25, wherein the cancer to be targeted is large bowel cancer.

31. The method according to claim 25, wherein the cancer to be targeted is gastric cancer.

32. The method of claim 25, wherein the immunomodulator is at least one selected from the group consisting of nivolumab and pembrolizumab.

33. A method for treating a cancer patient administered with a DNA function inhibitor, comprising:
administering an effective dose of an in to a subject in need thereof,
wherein the DNA function inhibitor is a combination drug comprising trifluridine and tipiracil hydrochloride in a molar ratio of 1:0.5, and
the immunomodulator is at least one selected from the group consisting of an anti-PD-1 antibody, and an anti-PD-L1 antibody, and an anti-PD-L2 antibody.

34. The method of claim 33, wherein the immunomodulator is at least one selected from the group consisting of nivolumab, pembrolizumab, atezolizumab, durvalumab, and avelumab.

35. The method of claim 33, wherein the immunomodulator is at least one selected from the group consisting of nivolumab and pembrolizumab.

36. The method according, to claim 33, wherein the dose per day of the combination drug is from 50 to 115% of the recommended dose when administered alone.

37. The method according to claim 33, wherein the dose per day of the combination drug is from 35 to 80 mg/m$^2$/day trifluridine.

38. The method according to claim 33, wherein the cancer to be targeted is gastrointestinal cancer, lung cancer, or breast cancer.

39. The method according to claim 33, wherein the cancer to be targeted is large bowel Cancer.

40. The method according to claim 33, wherein the cancer to be targeted is gastric cancer.

41. A method for treating a tumor in combination with using an immunomodulator, comprising:
administering an effective dose of a DNA function inhibitor to a subject in need thereof,
wherein the DNA function inhibitor is a combination drug comprising trifluridine and tipiracil hydrochloride in a molar ratio of 1:0.5, and
the immunomodulator is at least one selected from the group consisting of nivolumab, pembrolizumab, atezolizumab, durvalumab, and avelumab.

42. The method according to claim 41, wherein the dose per day of the combination drug is from 50 to 115% of the recommended dose when administered alone.

43. The method according to claim 41, wherein the dose per day of the combination drug is from 35 to 80 mg/m$^2$/day as trifluridine.

44. The method according to claim 41, wherein the cancer to be targeted is gastrointestinal cancer, lung cancer, or breast cancer.

45. The method according to claim 41, wherein the cancer to be targeted is large bowel cancer.

46. The method according to claim 41, wherein the cancer to be targeted is gastric cancer.

47. A method for treating a tumor in combination with using a DNA function inhibitor, comprising:
administering an effective dose of an immunomodulator to a subject in need thereof,
wherein the DNA function inhibitor is a combination drug comprising trifluridine and tipiracil hydrochloride in a molar ratio of 1:0.5, and
the immunomodulator is at least one selected from the group consisting of an anti-PD-1 antibody, and an anti-PD-L1 antibody and an anti-PD-L2 antibody.

48. The method of claim 47, wherein the immunomodulator is at least one selected from the group consisting of nivolumab, pembrolizumab, atezolizumab, durvalumab, and avelumab.

49. The method of claim 47, wherein the immunomodulator is at least one selected from the group consisting of nivolumab and pembrolizumab.

50. The method according to claim 47, wherein the dose per day of the combination drug is from 50 to 115% of the recommended dose when administered alone.

51. The method according to claim 47,
wherein the dose per day of the combination drug is from 35 to 80 mg/m²/day as trifluridine.

52. The method according to claim 47, wherein the cancer to be targeted is gastrointestinal cancer, lung cancer, or breast cancer.

53. The method according to claim 47, wherein the cancer to be targeted is large bowel cancer.

54. The method according to claim 47, wherein the cancer to be targeted is gastric cancer.

* * * * *

UNITED STATES PATENT AND TRADEMARK OFFICE
CERTIFICATE OF CORRECTION

| | | |
|---|---|---|
| PATENT NO. | : 11,612,653 B2 | Page 1 of 1 |
| APPLICATION NO. | : 16/068573 | |
| DATED | : March 28, 2023 | |
| INVENTOR(S) | : Norihiko Suzuki | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 299 days.

Signed and Sealed this
Seventh Day of January, 2025

Derrick Brent
*Acting Director of the United States Patent and Trademark Office*